(12) United States Patent
Sakamoto et al.

(10) Patent No.: US 7,082,810 B2
(45) Date of Patent: Aug. 1, 2006

(54) GAS SENSOR

(75) Inventors: Masashi Sakamoto, Aichi (JP);
Yoshikuni Sato, Aichi (JP); Keigo Banno, Aichi (JP); Katsuya Otake, Aichi (JP); Takeshi Morita, Aichi (JP); Hideki Ishikawa, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/379,710

(22) Filed: Mar. 6, 2003

(65) Prior Publication Data

US 2003/0177813 A1 Sep. 25, 2003

(30) Foreign Application Priority Data

Mar. 6, 2002 (JP) .......................... 2002-60683

(51) Int. Cl.
*G01N 29/02* (2006.01)

(52) U.S. Cl. ....................... 73/24.01; 73/24.01; 73/23.2; 73/24.04; 73/24.05; 73/24.06; 310/326; 310/327; 310/334; 310/335; 310/336; 310/337

(58) Field of Classification Search ................ 73/24.01, 73/23.02, 24.04, 24.05, 24.06, 23.2, 632; 310/334–337, 326–327
See application file for complete search history.

(56) References Cited

U.S. PATENT DOCUMENTS

| | | | | |
|---|---|---|---|---|
| 4,297,607 A | * | 10/1981 | Lynnworth et al. | ......... 310/334 |
| 5,060,514 A | * | 10/1991 | Aylsworth | ................ 73/24.01 |
| 5,313,820 A | * | 5/1994 | Aylsworth | ................ 73/24.01 |
| 5,351,522 A | * | 10/1994 | Lura | ........................ 73/24.01 |
| 6,311,573 B1 | * | 11/2001 | Bhardwaj | ................. 73/866.5 |
| 6,418,782 B1 | | 7/2002 | Sato et al. | |
| 6,449,563 B1 | | 9/2002 | Dukhin et al. | |

FOREIGN PATENT DOCUMENTS

| | | |
|---|---|---|
| EP | 0 661 536 A1 | 7/1995 |
| EP | 1 020 723 A2 | 7/2000 |
| JP | 2000-81421 | 3/2000 |
| JP | 2000-206099 | 7/2000 |

OTHER PUBLICATIONS

Myrna C. Sultan, et al. "Closed Loop Canister Purge Control System", SAE Technical Paper Series 980206, International Congress and Exposition, Detroit, Michigan, Feb. 23–26, 1998.

Masayuki Habaguchi, et al. "Gasoline Vapor Concentration Sensor—On Board Measurement by Ultrasonic Pulse", Proceedings for Society of Automotive Engineers of Japan 955, 1995–9, pp. 89–92.

* cited by examiner

*Primary Examiner*—Hezron Williams
*Assistant Examiner*—André K. Jackson
(74) *Attorney, Agent, or Firm*—Sughrue Mion, PLLC

(57) ABSTRACT

A gas sensor (10) including a measurement chamber (28) into which a gas GS is flown and a detection element main body (40) facing the measurement chamber (28). The detection element main body (40) includes an element case 42, and a protective film (48) is adhered to a bottom surface thereof. An acoustic matching plate (50) and a piezoelectric element (51) of a substantially columnar shape and a tube body (52) provided in a position surrounding the acoustic matching plate 50 and the piezoelectric element 51 are housed in the element case (42). A filler is then introduced into the element case (42), whereby the acoustic matching plate (50), the piezoelectric element (51), and the tube body (52) are sealed by a filled layer (99).

28 Claims, 18 Drawing Sheets

B-B Arrow View

Fig. 12 (A)

Experiment 1: Result

| Tube Body | | Hole | Reverberation ($\mu$ sec) |
|---|---|---|---|
| Absent | | — | 325 |
| Present<br><br>(Material: Cu + PET<br>Inner Diameter D: $\phi$ 9.8<br>Direction of Cu Surface:<br>Internal Surface) | 52A | Absent | 215 |
| | 52D | Lower | 270 |
| | 52C | Center | 263 |
| | 52B | Upper | 210 |

Fig. 12 (B)

Experiment 2: Result

| | Direction of Cu Surface | |
|---|---|---|
| 52E | External Surface | 275 |

Fig. 12 (C)

Experiment 3: Result

| Tube body | Inner Diameter | Reverberation ($\mu$ sec) |
|---|---|---|
| 52F | $\phi$ 12.7 | 232 |
| 52G | $\phi$ 14.5 | 251 |

Fig. 12 (D)

Experiment 4: Result

| Tube body | Inner Diameter | Reverberation ($\mu$ sec) |
|---|---|---|
| 52H | Al+PET | 247 |
| 52I | PET+Cu+PET | 281 |

|  | Tube Body | Plate-Like Body | Reverberation ($\mu$ sec) |
|---|---|---|---|
| (1) | Present (Cu+PET) | Absent | 210 |
| (2) |  | Present(Foamed Si) | 166 |
| (3) | Present (Foamed Si) | Absent | 218 |
| (4) |  | Present(Foamed Si) | 171 |

GAS SENSOR

BACKGROUND OF THE INVENTION

1. Technical Field of the Invention

The present invention relates to a gas sensor, and more specifically relates to a gas sensor which is provided facing a predetermined flow path of a gas and includes a detection element for receiving a predetermined signal to vibrate and detecting means which transmits a vibration wave generated by the vibration of the detection element in a flow path direction to detect characteristics of a gas.

2. Description of the Related Art

Conventionally, a gas sensor is known which detects, for example, a concentration, a temperature, or a humidity of a specific component as characteristics of a gas present in a flow path, using a detection element. In such a gas sensor, a signal from the detection element is electrically processed and output as an electric signal corresponding to the characteristics of the gas. As an example of the gas sensor, a gas concentration sensor which is provided in transportation equipment mounted with an internal combustion engine such as an automobile and which detects a concentration of gasoline, gas oil, or the like utilizing a change in propagation speed of a vibration wave of sound will be discussed.

Such a gas sensor is arranged, for example, in a passage for purging gasoline from a canister mounted on the automobile to an inlet pipe of the internal combustion engine. The gas concentration sensor includes a flow path of a predetermined volume through which a gas containing gasoline vapor in the above-described passage flows and a detection element which is provided facing this flow path and detects a gas concentration. The gas concentration sensor vibrates the detection element in detecting the gas concentration and transmits a vibration wave (e.g., ultrasonic wave) generated by this vibration in a flow path direction. Such a vibration wave, which is transmitted in the flow path direction of the gas from the detection element by the detection element vibrating for detection of the gas concentration, is hereinafter referred to as a vibration wave for detection. The speed of the vibration wave passing through the flow path changes according to a concentration of gasoline vapor existing in the flow path. The gas concentration sensor detects the speed of the vibration wave for detection passing through a flow path of a fixed flow path length with a receiver for receiving the vibration wave for detection, finds the concentration of the gasoline vapor as a result of this detection, and outputs it.

In such a conventional gas sensor, the detection element for transmitting the vibration wave for detection is arranged in a housing which is formed of resin or the like having high heat resistance (e.g., see JP-A-2000-206099). In addition, since it is necessary to keep a position of the detection element constant in order to accurately detect the speed of the vibration wave for detection passing through the gas flow path, a filled layer is formed by filling a filler such as urethane in the housing, in which the detection element is arranged, to seal the detection element and regulate a positional movement of the detection element.

3. Problems Solved by the Invention

However, in such a gas sensor for detecting a gas concentration utilizing a vibration wave from a detection element, reverberation may occur in a filled layer in which the detection element is embedded following vibration of the detection element, and as the detection element is affected by this reverberation, it is likely that characteristics of a gas such as a gas concentration cannot be detected accurately.

That is, in the case in which a detection element is used both for transmission and reception, it is likely that, if a reverberation in the filled layer lasts a long time, a vibration wave emitted in a direction different from the transmission direction of the vibration wave for detection by vibration of the detection element affected by this reverberation (hereinafter referred to as noise vibration wave) interferes with the vibration wave for detection, and accurate detection of a gas concentration based upon the vibration wave for detection cannot be performed. In addition, in the case in which the element for transmission and the element for reception are provided separately, it is also likely that, if a reverberation in the filled layer lasts a long time, after a vibration wave for detection is transmitted to a gas flow path, a noise vibration wave is transmitted to the gas flow path from the detection element affected by the reverberation, and accuracy of detection of a gas concentration based upon the vibration wave for detection falls.

The present inventors observed that such reverberation continues over a longer period at higher temperatures. Therefore, in an environment in which temperature tends to increase such as in the vicinity of a passage for purging gasoline or a gas flow path in the gas sensor, reverberation may increase to make accurate detection of gas concentration difficult.

In addition, in a conventional gas sensor, it is likely that, in the case in which temperature increases in the gas sensor, the filler in the housing thermally expands and a position of the detection element moves in the housing following this thermal expansion. In the case in which such positional movement occurs, since a flow path length of the gas flow path changes and the time for the vibration wave for detection passing through the gas flow path changes following the change in the flow path length, it is likely that accuracy of detection of a gas concentration based upon the vibration wave for detection falls.

SUMMARY OF THE INVENTION

It is therefore an object of the present invention to adopt a structure as described below for the purpose of solving at least one of the above-described problems of the prior art, and to provide a gas sensor which is capable of accurately detecting a gas concentration at high temperature.

The above objects have been achieved by providing a gas sensor including detection element provided facing a predetermined flow path of a gas and which receives a predetermined signal to vibrate, and detecting means which transmits a vibration wave, which is generated by vibration of the detection element in the flow path direction, as a vibration wave for detection to detect characteristics of the gas, the gas sensor comprising:

a housing for housing the detection element in a form capable of transmitting the vibration wave for detection in the flow path direction;

an attenuation member which is provided in the housing and with which the vibration wave emitted in a direction different from the transmitting direction of the vibration wave for detection collides to attenuate an energy thereof; and a filled layer which is formed by filling a predetermined filler in the housing at least up to a position where the detection element is embedded.

According to the gas sensor of the above-described structure, the element for transmitting a vibration wave for detection in a flow path direction of a gas according to vibration and an attenuation member with which vibration wave (noise vibration wave) emitted in a direction different from a transmission direction of the vibration wave for detection collides to have an energy thereof attenuated are provided in the housing, and the filled layer is formed by filling the predetermined filler at least up to a position where the detection element is embedded in the housing. Consequently, in the case in which a reverberation occurs in the filled layer following the transmission of the vibration wave for detection due to vibration of a detection element having received a predetermined signal, a noise vibration wave emitted by the vibration of this element for detection affected by the reverberation collides with the attenuation member to have an energy thereof attenuated. Consequently, reverberation generated in the filled layer promptly decreases and duration of the reverberation is reduced. Therefore, accurate detection of characteristics of the gas based upon the vibration wave for detection can be secured.

The attenuation member is preferably set in a propagation route of noise vibration wave to be emitted in term of increasing certainty of collision with the noise vibration wave. As an example of a set position of the attenuation member, a position surrounding the detection element between the housing and the detection element, a surface of the element for detection opposite a surface of the filled layer, and the like are possible. The attenuation member set in the former position is hereinafter referred to as an intervening member and the attenuation member set in the latter position is hereinafter referred to as a surface member. In this case, a structure in which one of the intervening member and the surface member is set may be adopted or a structure in which both the intervening member and the surface member are set may be adopted. It is also possible to set the attenuation member in a position other than the above-mentioned position cited as an example.

In the case in which the above-mentioned intervening member is provided as the attenuation member, since an energy of a noise vibration wave emitted in a direction of an internal peripheral surface of the housing is attenuated by collision with the intervening member, reverberation generated in the filled layer can be reduced promptly. By adopting a structure in which this intervening member surrounds the entire periphery of the element for detection, the attenuation efficiency of reverberation can be further increased.

It was also found that, if the intervening member was formed using plural media with different densities, reverberation was further reduced in duration. If such a structure is adopted, it is possible that a noise vibration wave generated in the filled layer tends to be reflected by the intervening member, and the attenuation efficiency of an energy of the noise vibration wave increases. Therefore, reverberation can be reduced early after its generation.

The intervening member is desirably constituted by using a medium having a larger density than the filler on the detection element side. In this way, the attenuation efficiency of a reverberation can be further increased. More specifically, for example, a structure is possible in which the medium used in the housing side is a synthetic resin and the medium used on the detection element side is a metal.

In the case in which a metal is used on the detection element side of the intervening member, the metal preferably does not adhere to the filled layer. In this manner, since a metal surface of the intervening member is allowed to slide against the filled layer, thermal stress generated in the periphery of the detection element is eased. In addition, since an interface in which the metal and the filled layer are not adhered to each other exists, a loss of energy of the noise vibration wave occurs on the interface. Therefore, the duration of the reverberation can be further reduced. A structure in which the intervening member has a predetermined number of holes may be adopted.

It is also preferable to form the intervening member with a porous body. As such a porous body, foamed silicon, foamed urethane, foamed rubber, porous ceramics, porous carbon, and the like are possible. By using such a porous body, the attenuation efficiency of an energy of a noise vibration wave increases, and a gas sensor with a short duration of a reverberation can be realized.

The gas sensor may have a structure in which the intervening member is arranged in a position adjacent to the detection element. In the case in which this structure was adopted, the present inventors found that the attenuation efficiency of the noise vibration wave further increased and reverberation could be reduced more promptly.

A structure may be added in which a film which is mounted on an opening portion of a housing and partitions the housing and a flow path is provided, a matching member which is mounted on the film and transmits vibration of an element for detection to a flow path via the film and a detection element mounted on a surface on the opposite side of the mounting surface of the matching member on the film are housed in the housing, and an intervening member is provided in a position surrounding the element for detection and the matching member between the matching member and detection element and the housing (hereinafter referred to as "structure with a film"). In this structure with a film, in the case in which the intervening member is arranged in a position adjacent to the detection element, the detection element becomes less likely to be affected by thermal expansion of the filled layer, and positional movement of the detection element following thermal expansion of the filled layer (e.g., the detection element moves in a direction toward a flow path of a gas) can be prevented surely. Therefore, accuracy of detection of characteristics of the gas can be further improved.

In addition, in the structure with a film, in the case in which the metal used on the detection element side of the intervening member is made so as not to adhere to the filled layer, it is also preferable to form plural holes in the intervening member. The plural holes are offset to the side opposite the flow path side of the intervening member. In this way, the positional movement of the detection element following thermal expansion of the filled layer is suppressed by the holes provided in the intervening member. At the same time, the holes are offset to the side opposite the flow path side, whereby appropriate slip of the metal surface of the intervening member against the filled layer is secured, and the thermal stress generated in the periphery of the detection element is eased. Therefore, the duration of reverberation can be further reduced while securing accuracy of detection of characteristics of the gas.

In the case in which the above-mentioned surface member (which is provided on the surface of the detection element opposite the surface of the filled layer) is provided as the attenuation member, since the energy of the noise vibration wave emitted in the surface direction of the filled layer is attenuated by colliding with the surface member, reverberation generated in the filled layer can be reduced promptly. In addition, in the case in which both the intervening member and the surface member are provided, since the attenuation efficiency of the energy of the noise vibration wave becomes higher than that in the case in which one of them is provided, the reverberation can be reduced more promptly and the duration of the reverberation can be further reduced.

It is also desirable to adhere and fix the surface member to the detection element. In this way, in the case in which the filled layer expands following increase in an ambient temperature, the surface member exfoliates from the surface of the detection element, whereby a gas layer (foams) is less likely to be generated between the detection element and the surface member. As a result, the duration of the reverberation and sensitivity of the detection element never change largely with the detection element subjected to local stress by the generation of such foams. Therefore, characteristic change of the gas sensor following an increase in the ambient temperature can be suppressed.

It is also preferable to form the surface member with a porous body. In this way, the attenuation efficiency of the energy of the noise vibration wave increases, and a gas sensor having a short duration of reverberation can be realized.

It is also desirable to adopt a structure in which at least a part of the porous body is embedded in the filled layer and filler penetrates into the inside of the porous body. In this way, the filler filled in the housing penetrates into foams inside the porous body, and an interface between the porous body and the filler increases in the porous body. Therefore, the attenuation efficiency of the energy of the noise vibration wave in the interface increases, and the reverberation time can be further reduced. In addition, the characteristic change of the gas sensor following an increase in ambient temperature can be suppressed. For example, in the case in which the filled layer expands following an increase in ambient temperature, the duration of reverberation and the sensitivity of the detection element never change largely with the detection element subjected to local stress due to increase in an air volume in the porous body.

The gas sensor may have a structure in which a reflecting section for reflecting a vibration wave, which is transmitted from one detection element in the flow path direction, in the direction of the one detection element is provided, and the one detection element receives the vibration wave reflected by the reflecting section, thereby detecting characteristics of the gas. In other words, this is a structure in which one detection element which has transmitted the vibration wave for detection in the flow path direction receives the vibration wave for detection reflected by the reflecting section after the transmission, thereby detecting characteristics of the gas. In the case in which this structure is adopted, again, as a result of an energy of a noise vibration wave being attenuated by the above-described action of the attenuation member, reverberation promptly attenuates and the duration of the reverberation is reduced. Therefore, inaccurate detection of the characteristics of the gas can be prevented while making the structure for detecting characteristics of a gas simple. For example, it becomes possible to avoid a situation in which, after a vibration wave for detection is transmitted toward a flow path of a gas by vibrating one detection element, a noise vibration wave with a large energy is transmitted from this one detection element and this noise vibration wave interferes with the vibration wave for detection reflected by the reflecting section, and accuracy of the vibration wave for detection received by the one element for detection can be secured.

BRIEF DESCRIPTION OF THE DRAWINGS

FIGS. 12(A) to 12(D) are explanatory tables showing results of experiments 1 to 4 concerning the first embodiment.

DESCRIPTION OF REFERENCE NUMERALS AND SYMBOLS

Figure 1:
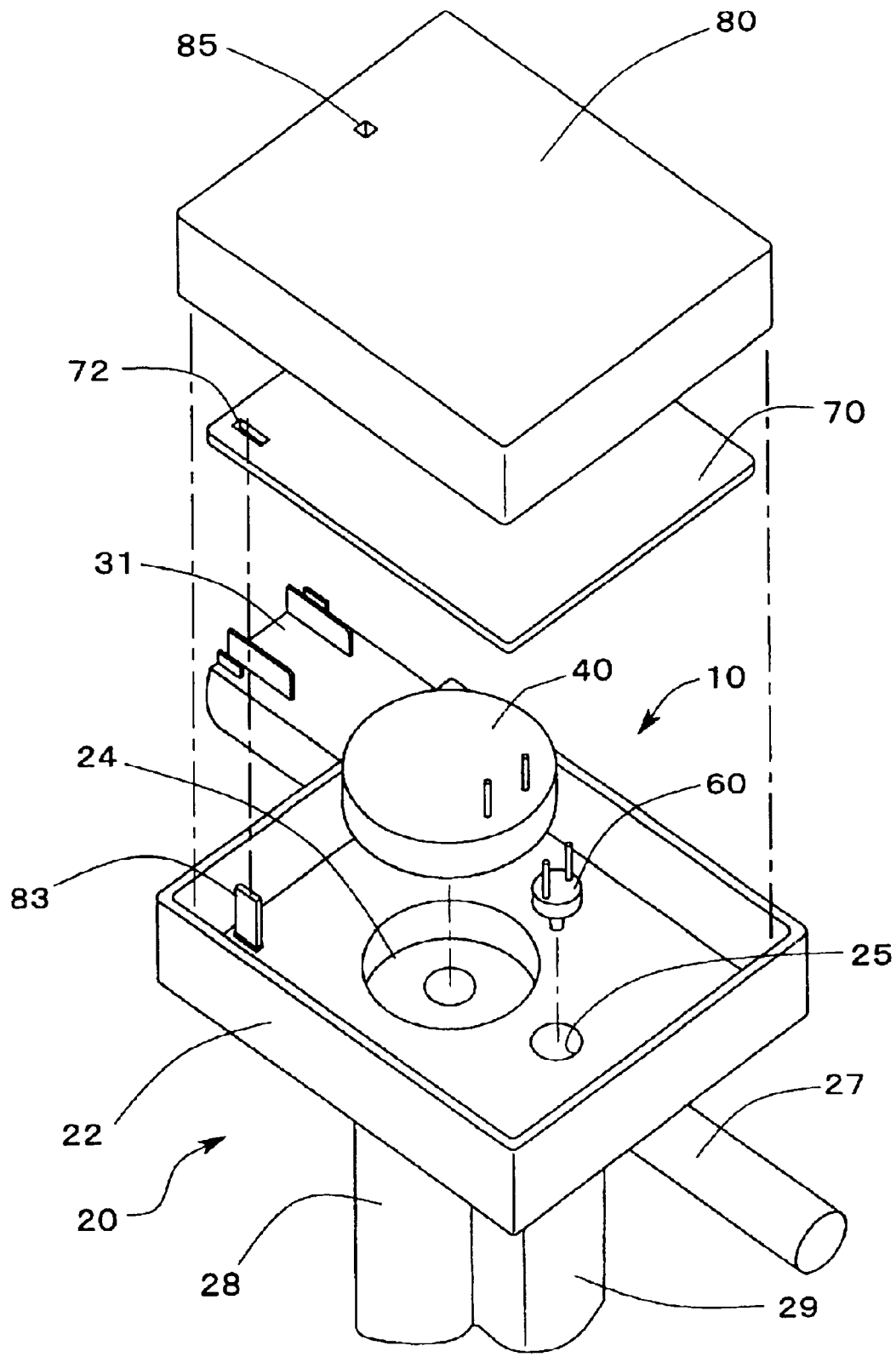
FIG. 1 is an explanatory view showing a disassembled perspective shape of a gas sensor 10 as an embodiment of the present invention.

10 . . . Gas sensor
20 . . . Flow path forming member
22 . . . Housing section
22a. . . Projected portion for terminal
24 . . . Recessed portion
24a . . . Communication hole
25 . . . Insertion hole
27 . . . Introducing path
28 . . . Measurement chamber
29 . . . Bypass flow path
31 . . . Connector
31a to 31d . . . Terminals
32 . . . Introducing hole
33 . . . Reflecting section 34 . . . Outlet
35 . . . Discharge flow path
36 . . . Metal plate
37 . . . Recessed portion
38 . . . Opening portion
40, 140, 240 . . . Detection element main bodies
41, 141, 241 . . . Flange sections
42, 142, 242 . . . Element cases
43, 143, 243 . . . Housing sections
45, 145, 245 . . . End faces
46, 146 . . . Step portions
48, 148, 248 . . . Protective Films
50, 150, 250 . . . Acoustic matching plates
51, 151, 251 . . . Piezoelectric elements
52, 52A to 52I, 152, 252Q . . . Tube bodies
52a, 152a . . . Polyethylene terephthalate films
52b, 152b . . . Adhesion layers
52c, 152c . . . Copper foils
53 . . . Openings
54a, 54b, 154a, 154b, 254a, 254b . . . Lead wires
55a, 55b, 155a, 155b 255a, 255b . . . Terminals
56a, 56b, 156a, 156b, 256a, 256b . . . Projecting portions
59, 159, 259 . . . Projections
60 . . . Thermistor
70 . . . Electronic circuit substrate
72 . . . Attachment hole
80 . . . Case
83 . . . Cut-raised portion
85 . . . Insertion hole
88 . . . Cushion material
91 . . . Microprocessor
92 . . . D/A Converter
93 . . . Driver
96 . . . Amplifier
97 . . . Comparator
99, 199, 299 . . . Filled layers
151a . . . Positive electrode
151b . . . Negative electrode
151c . . . Folded-back portion
165Q, 265Q . . . Plate-like bodies
165Qe . . . Surface
DW . . . Ultrasonic wave for detection
NW, NWs, NWu . . . Noise ultrasonic waves

DETAILED DESCRIPTION OF THE PREFERRED EMBODIMENTS

The invention will now be described in greater detail by reference to the accompanying drawings and embodiments. However, the present invention should not be construed as being limited thereto.

A. First Embodiment

FIG. 1 is a disassembled perspective view of a gas sensor 10 as a first embodiment of the present invention. This gas sensor 10 is a sensor for detecting a concentration of gasoline vapor utilizing the fact that a propagation speed of an ultrasonic wave changes according to a gas concentration. This gas sensor is arranged, for example, in a passage for purging gasoline from a canister, which is mounted on a vehicle using an internal combustion engine as a power source, to an inlet passage and used for the purpose of detecting a concentration of the gasoline to be purged, and the like.

A-1. Overall Structure of the Gas Sensor

As shown in FIG. 1, roughly speaking, this gas sensor 10 includes: a flow path forming member 20 for forming a flow path through which gasoline vapor as an object of concentration detection passes; a detection element main body 40 which is housed in a housing section 22 integrally formed in this flow path forming member 20; a thermistor 60 for detecting a temperature of a gas passing through the flow path; an electronic circuit substrate 70 arranged above the detection element main body 40; and a metal case 80 to be fit in the housing section 22.

The flow path forming member 20 is formed of a synthetic resin containing a glass filler. Elasticity of the flow path forming member 20 is adjusted to a value suitable for use as a gas sensor. In addition, the detection element main body 40 is fixed to a recessed portion for attachment 24 provided in the housing section 22 by ultrasonic welding, and the thermistor 60 is inserted in and fixed to an insertion hole for attachment 25.

As discussed below, the detection element main body 40 and the thermistor 60 have a terminal for exchanging electric signals. This terminal is inserted in a corresponding attachment hole of the electronic circuit substrate 70 and fixed by soldering.

The gas sensor 10 is manufactured by, after fixing the detection element main body 40 and the thermistor 60 to the housing section 22, attaching the electronic circuit substrate 70 to the housing section 22, further fitting the case 80 in the housing section 22, and then molding them with resin, for example, urethane resin.

A-2. Structure of the Flow Path Forming Member 20

As shown in FIG. 1, this flow path forming member 20 is provided with the housing section 22 for housing the detection element main body 40 above it and has a flow path through which a gas for detection of a concentration flows below the housing section 22. This flow path includes an introducing path 27 for introducing a gas containing gasoline vapor (hereinafter referred to as gas GS) into the gas sensor 10, a measurement chamber 28 for detecting a concentration of the gasoline vapor in this gas GS with an ultrasonic wave, and a bypass flow path 29 for bypassing the gas GS away along the measurement chamber 28. The measurement chamber 28 and the bypass flow path 29 are provided substantially directly below the detection element main body 40 and substantially directly below the thermistor 60, respectively.

Figure 2:
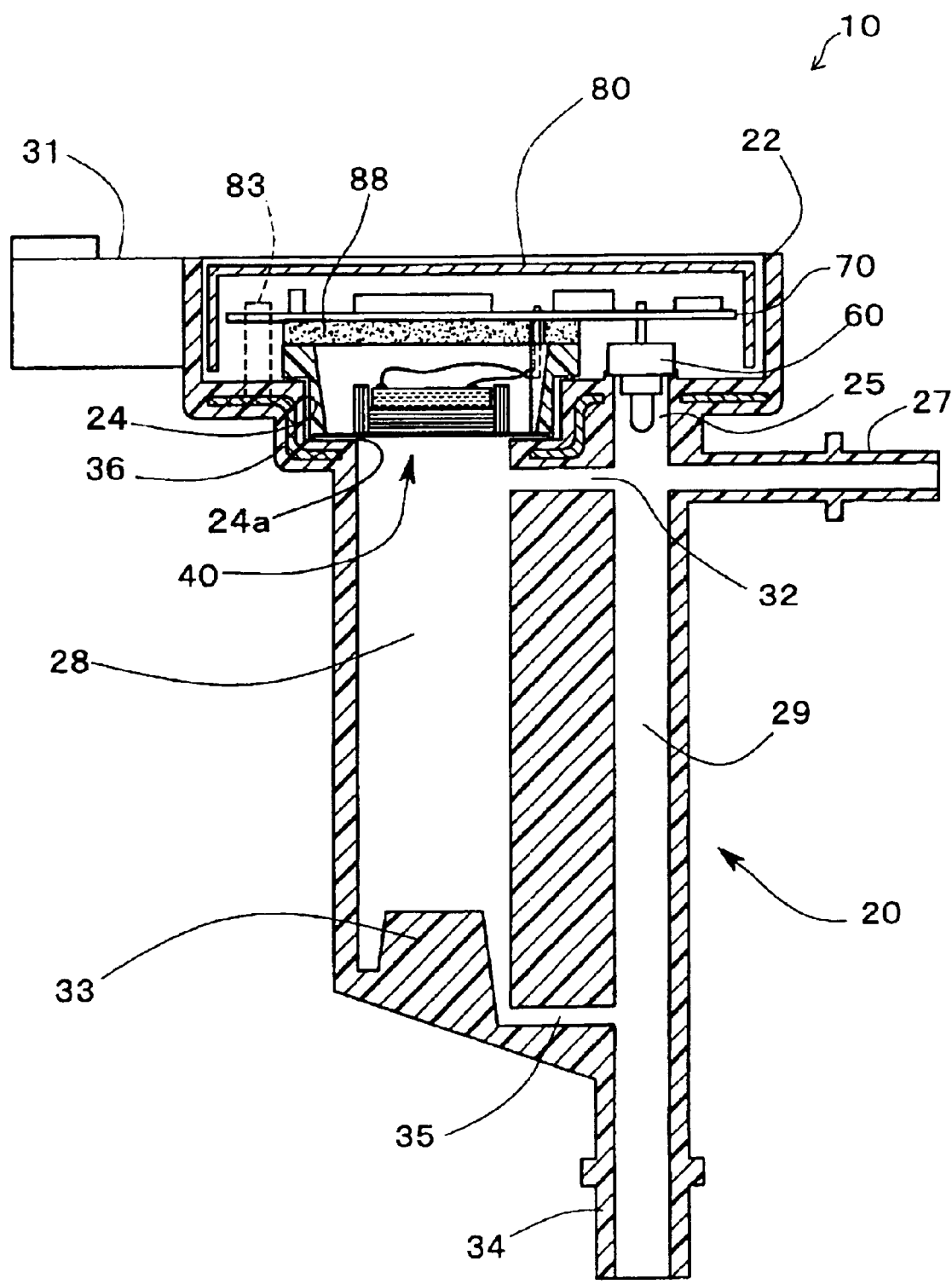
FIG. 2 is an explanatory view showing a vertical section of the gas sensor 10.

In order to describe such a flow path structure in detail, a vertical section of the gas sensor 10 is shown in FIG. 2. FIG. 2 is a sectional view of the gas sensor 10 cut along a plane including axial lines of the introducing path 27 and the detection element main body 40. As shown in FIG. 2, a flow path of the gas GS formed inside the flow path forming member 20 is divided into the introducing path 27, the measurement chamber 28, and the bypass flow path 29. The introducing path 27 extended in a substantially horizontal direction communicates with the bypass flow path 29 at a right angle and also communicates with the measurement chamber 28 via an introducing hole 32.

In this embodiment, the above-described measurement chamber 28 is referred to herein as a "predetermined flow path of a gas". It is also possible to realize the "predetermined flow path of a gas" in a form other than this measurement chamber 28.

As shown in FIG. 2, an outlet 34 is formed in a lower part of the bypass flow path 29. In this embodiment, the outlet 34 is connected to the inlet passage of the internal combustion engine by a hose (not shown). The gas GS introduced from the introducing path 27 is discharged to the inlet passage from the above-described outlet 34.

As shown in FIGS. 1 and 2, an insertion hole 25 is formed at an end on the opposite side of the outlet 34 of the bypass flow path 29, and the thermistor 60 is attached to this insertion hole 25. The thermistor 60 detects a temperature of the gas GS flowing into the bypass flow path 29 from the introducing path 27 via the insertion with the insertion hole 25.

As shown in FIGS. 1 and 2, an upper part of the measurement chamber 28 communicates with the recessed portion 24 via a communication hole 24a formed on a bottom surface of the recessed portion 24, and the detection element main body 40 is attached to this recessed portion 24. The detection element main body 40 detects a concentration of the gasoline vapor in the gas GS flowing into the measurement chamber 28, via the communication hole 24a. In this case, the concentration of the gasoline vapor is detected with a predetermined relationship with the detected temperature of the gas GS.

As shown in FIG. 2, a reflecting section 33 for reflecting an ultrasonic wave transmitted from the detection element main body 40 is formed below the measurement chamber 28. The function of this reflecting section 33 will be described later.

The reflecting section 33 is formed by raising a central area of the bottom of the measurement chamber 28 by a predetermined distance (several millimeters in this embodiment). Consequently, a predetermined gap is formed around the reflecting section 33. The gap around this reflecting section 33 is directly connected to the bypass flow path 29 via a discharge flow path 35 communicating with the bottom of the measurement chamber 28. Consequently, the gas GS flowing in from the introducing path 27 through the introducing hole 32 fills inside the measurement chamber 28 and exits to the bypass flow path 29 from the discharge flow path 35 at a predetermined ratio.

Note that, since the discharge flow path 35 is provided in the bottom of the measurement chamber 28, in the case in which water vapor, gasoline vapor, or the like in the measurement chamber 28 is condensed and liquefied, the discharge flow path 35 also functions as a drain for discharging water drips or oil drips.

Figure 3:
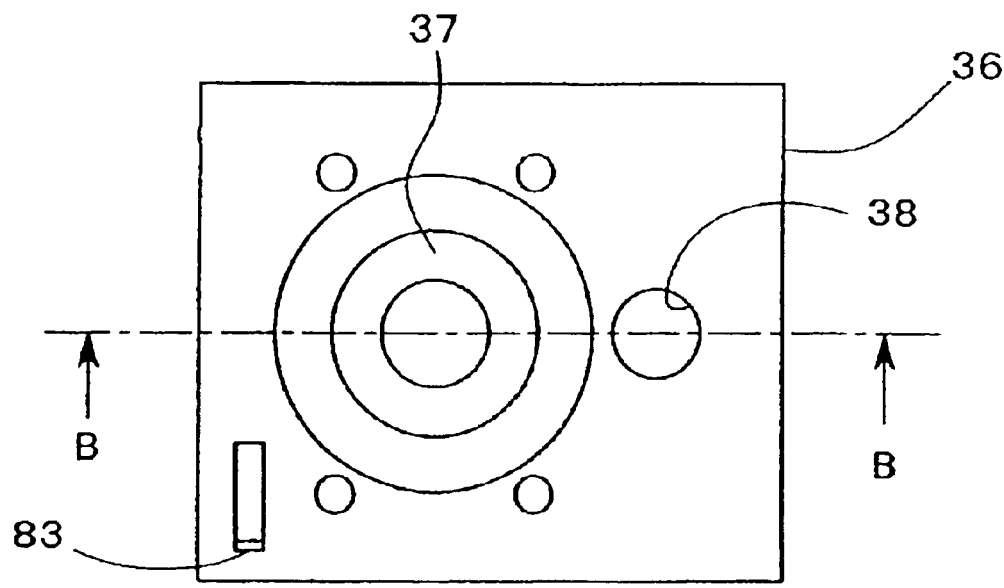
FIGS. 3(A) to 3(C) are explanatory views showing a shape of a metal plate 36 inserted in a housing section 22.
Figure 3:
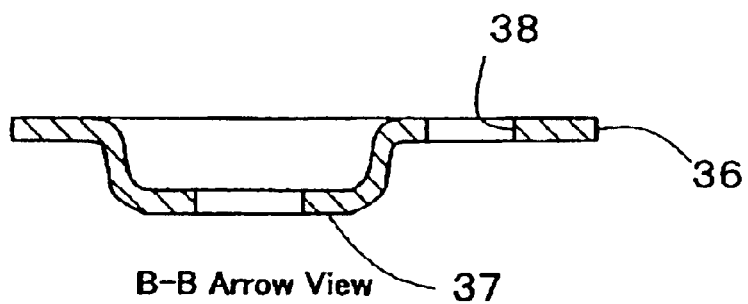
Figure 3:
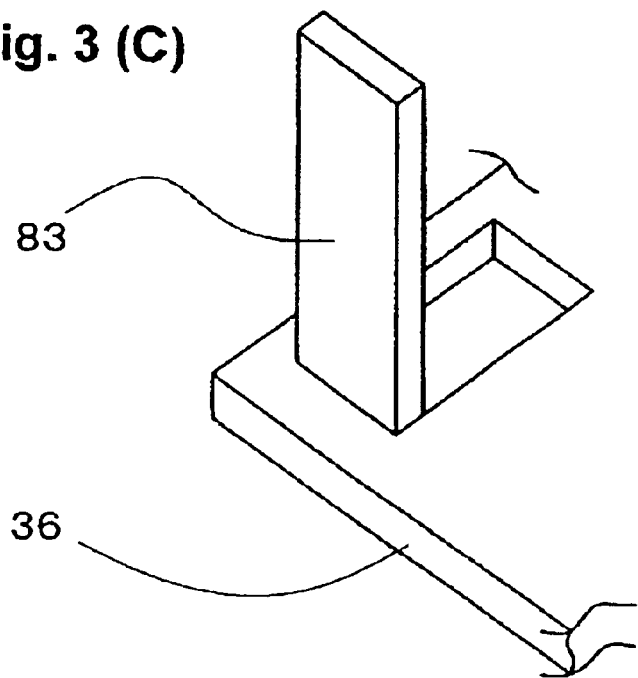

As described above, in the housing section 22 of the flow path forming member 20, the recessed portion for attachment 24 provided with the communication hole 24a communicating with the measurement chamber 28, the insertion hole 25 for attaching a thermistor, and the like are formed. A metal plate 36 shown in FIG. 3 is insert-molded in a place corresponding to the housing section 22. As shown in FIG. 3, this metal plate 36 has a shape substantially following a bottom surface shape of the housing section 22 and has a recessed portion 37 corresponding to the recessed portion 24, and an opening portion 38 corresponding to the insertion hole 25. The metal plate 36 includes a cut-raised portion 83 at its one corner. As shown in FIG. 1, after being insert-molded, this cut-raised portion 83 is brought into a state in which it is vertically provided on the inner side of the housing section 22 and, when the electronic circuit substrate 70 is attached, inserted in an attachment hole 72 on the substrate. A land connected to a ground line is prepared in the attachment hole 72, and the cut-raised portion 83 is soldered to this land.

Figure 4:
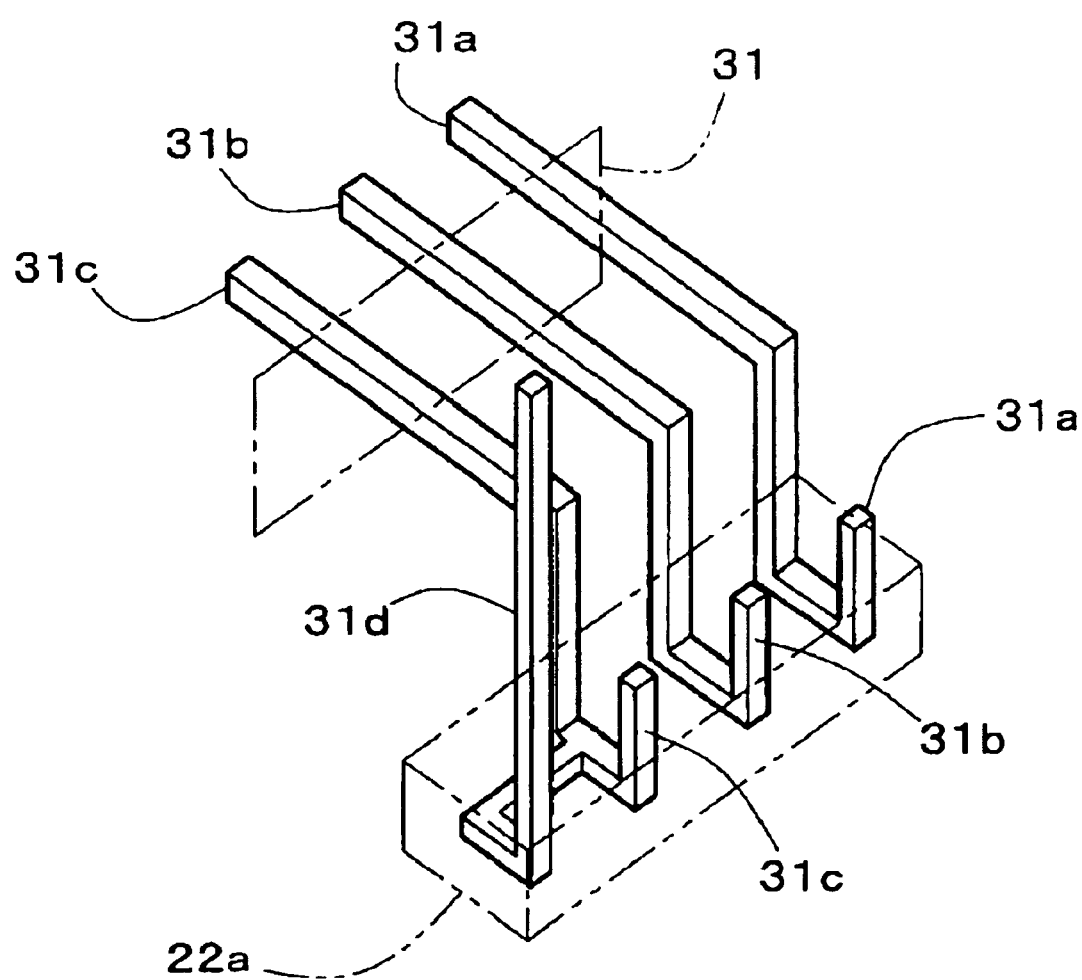
FIG. 4 is a perspective view showing shapes of terminals 31a to 31d provided in a connector 31.

In one part adjacent to the cut-raised portion 83 among four inside corners of the housing section 22, a projected portion for terminal 22a is provided which is also used as a support base for mounting the electronic circuit substrate 70. On the outside thereof, a connector 31 for exchanging an electric signal is formed, and terminals forming the connector 31 penetrate through an external wall of the housing section 22 in this part. Three terminals are prepared for the connector 31 on its entrance side, and two terminals on both sides of the three terminals serve as power supply lines (ground and DC voltage Vcc) for supplying power to the gas sensor 10 from the outside and the one in the center thereof serves as a signal output line from the gas center 10. The number of the terminals of this connector 31 is four (31a to 31d) as shown in FIG. 4 on the housing section 22 side. This is because, as shown in the figure, the terminal 31c for the ground line has a shape branched into two in the middle. One of the two branched terminals 31d is extended upward and inserted in an insertion hole 85 prepared in a corresponding position of the case 80 when the case 80 is assembled. After insertion, terminal 31d is soldered or brazed to the case 80. As a result, the entire case 80 is electrically coupled to the ground line. In the remaining two parts among the corners of the housing section 22, a support base (now shown) is formed for mounting the electronic circuit substrate 70.

A-3. Structure of the Detection Element Main Body 40

Figure 5:
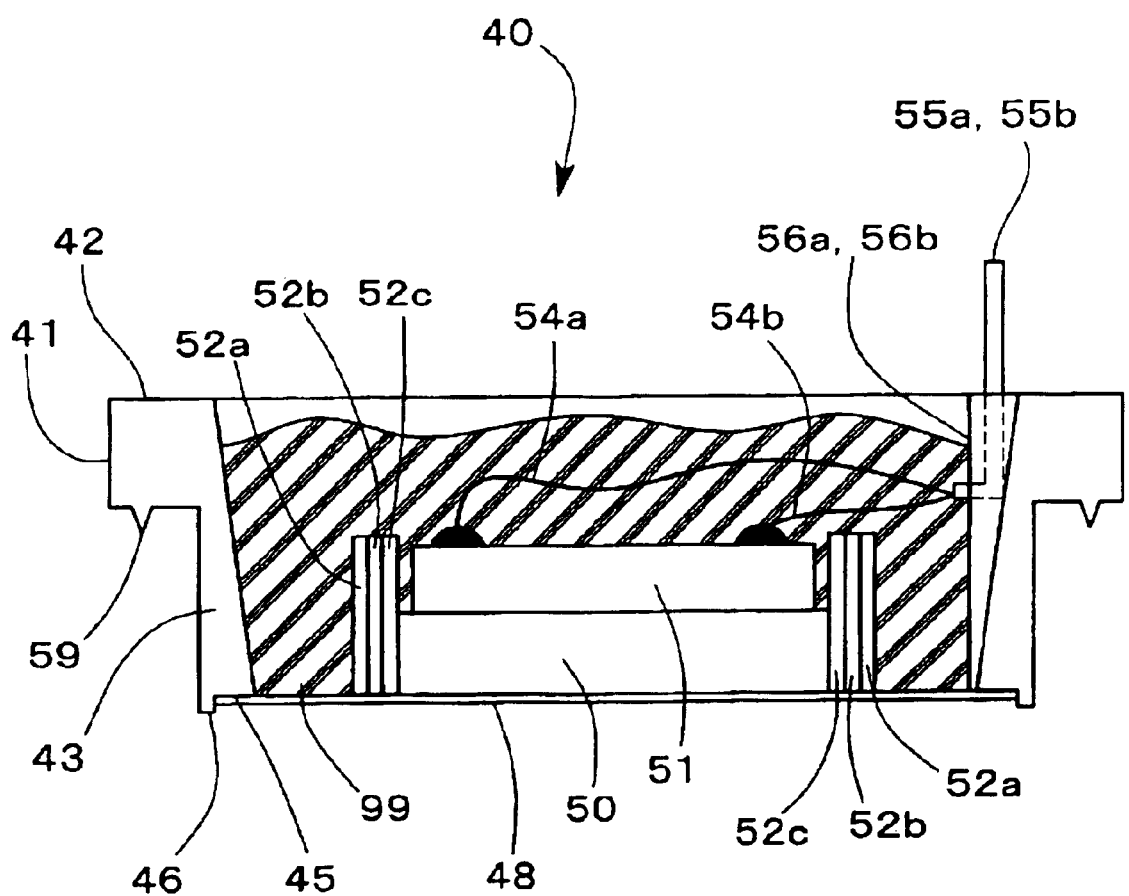
FIG. 5 is a sectional view showing a structure of a detection element main body 40.

A structure of the detection element main body 40 is shown in a sectional view of FIG. 5. As shown in FIG. 5, the detection element main body 40 includes an element case 42 made of synthetic resin. An opening portion is provided on a bottom surface of this element case 42, and a circular protective film 48 using a material having an anti-gasoline property is adhered to an end face 45 around this opening portion so as to cover the opening portion. Note that a step portion 46 is formed in an outside edge of the end face 45.

In this embodiment, the above-mentioned element case 42 to which the protective film 48 is referred to herein as a "housing". It is also possible to realize a "housing" in a form other than this element case 42 to which the protective film 48 is adhered.

The element case 42 includes a flange section 41 of a shape extended to the outside above it and a housing section 43 below the flange section 41. The flange section 41 is formed in diameter larger than the recessed portion 24 provided in the housing section 22, and the housing section 43 is formed in a diameter smaller than the recessed portion 24. A projection for welding 59 is formed in a circular shape substantially in the center of a lower surface of the flange section 41.

As shown in FIG. 5, the element case 42 has a sectional shape of a substantially reverse "L". An internal peripheral surface of the element case 42 is tapered at approximately 11 degrees with respect to a vertical surface. Therefore, a part corresponding to the external wall of the housing section 43 becomes thicker as it is closer to the lower part, that is, the protective film 48. As a result, the housing section 43 of the element case 42 has an external wall which is thin and has excellent flexibility in the vicinity of its joint with the flange section 41, and on the end face 45 on the lower side, has an area sufficient for attaching the protective film 48.

Projecting portions 56a and 56b of a shape projecting to an inner side of the case are provided in the element case 42, and terminals 55a and 55b are embedded in these projecting portions 56a and 56b. As shown in FIG. 5, one end of each of the terminals 55a and 55b is slightly projected to the inner side of the case, and the other end of each of the terminals 55a and 55b is projected above the case.

As shown in FIG. 5, an acoustic matching plate 50 of a substantially columnar shape, a piezoelectric element 51, and a tube body 52 are housed in the element case 42. In this embodiment, the above-mentioned acoustic matching plate 50 is referred to herein as a "matching member". The acoustic matching plate 50 is adhered and fixed to substantially a center of the protective film 48, and a piezoelectric element 51 is adhered and fixed to substantially a center of an upper surface of this acoustic matching plate 50. The acoustic matching plate 50 is provided for transmitting vibration of the piezoelectric element 51 into the air (to the measurement chamber 28 in this embodiment) efficiently via the protective film 48. Vibration of the piezoelectric element 51 can be efficiently transmitted into the measurement chamber 28 as an ultrasonic wave by joining the piezoelectric element 51 to the protective film 48 via the acoustic matching plate 50 rather than adhering it directly thereto. This is because an ultrasonic wave easily reflects in a place where there is a difference of densities of media. Although a plate formed by hardening a large number of small glass balls with epoxy resin was used as the acoustic matching plate 50 in this embodiment, it is possible to use other materials.

The piezoelectric element 51 is an electrostrictive element such as piezoelectric formed in a columnar shape and is cut out with directions of gratings arranged such that distortion occurs only in an axial direction when a voltage is applied to electrodes formed on its upper and lower surfaces in the axial direction. As such a piezoelectric element 51, a crystal such as a piezoelectric ceramic or a rock crystal can be used appropriately. Note that, although not specifically illustrated, the electrodes may be formed with a technique such as vapor deposition on the upper and lower surfaces of the piezoelectric element 51 or may be formed by adhering a metal thin plate to the piezoelectric element 51.

One end of each of the two lead wires 54a and 54b is soldered to respective electrodes of the piezoelectric element 51. As shown in FIG. 5, the other end of each of the two lead wires 54a and 54b is soldered to one end of the respective terminals 55a and 55b projecting from the projecting portion 56a and 56b of the element case 42.

As described below, the piezoelectric element 51 functions as a transmitter for transmitting an ultrasonic wave into the measurement chamber 28 and, at the same time, in this embodiment, also functions as a receiver for receiving ultrasonic vibration and outputting an electric signal. It is also possible to separately provide an element for transmission and an element for reception in making a gas sensor.

In addition, a tube body 52 of cylindrical shape is mounted on the protective film 48 in a position where it surrounds the acoustic matching plate 50 and the piezoelectric element 51. This tube body 52 is formed by rolling a polyethylene terephthalate film 52a and a copper foil 52c, which are adhered together via an adhesion layer 52b, in a tubular shape with the copper foil 52c side being inside to fit and adhere end faces on both sides together. Details of this tube body 52 will be described later.

After housing and mounting the acoustic matching plate 50, the piezoelectric element 51, and the tube body 52 in the element case 42 to which the protective film 48 is adhered in this manner, the lead wires 54a and 54b of the piezoelectric element 51 are connected to the terminals 55a and 55b. After this connection, resin is filled in the element case 42 as a filler, whereby a filled layer 99 is formed in the element case 42 as shown in FIG. 5. As a result, the acoustic matching plate 50, the piezoelectric element 51, the tube body 52, the lead wires 54a and 54b are brought into a state in which they are embedded in the filled layer 99. Consequently, assembly of the detection element main body 40 is completed. Note that urethane is used as the filler in this embodiment.

In this embodiment, the above-described tube body 52 is referred to herein as an "intervening member". It is also possible to realize an "intervening member" in a form other than the tube body 52. In addition, in this embodiment, the above-described filled layer 99 is referred to herein as a "filled layer". It is also possible to realize a "filled layer" in a form other than this filled layer 99.

According to such assembly, the detection element main body 40 is formed in a disk shape as shown in FIG. 1. After completing the assembly, the flange section 41 of the element for detection main body 40 is adhered to the recessed portion 24 of the housing section 22 firmly by ultrasonic welding the projection 59 formed on a lower surface of the flange section 41.

Turning back briefly to FIG. 2, a cushion material 88 may be provided in the flow path forming member 20 in the vicinity of the detection element main body 40. The cushion material 88 is comprised of porous silicone, so as to prevent reverberation of the piezoelectric element 51 which reverberation tends to occur if another acoustically different filler made of urethane resin is filled in the housing section 22 to contact inner filler 99. Insertion of such porous material limits air between the fillers, thereby preventing the air to change greatly in volume as a function of temperature as well as preventing thermal stress affecting the filler 99 and the piezoelectric element 51.

A-4. Structure of the Electronic Circuit Substrate 70 and a Technique for Detecting Vapor Concentration of Gasoline Next, a structure of the electronic circuit substrate 70 and attachment thereof will be described. The electronic circuit substrate 70 is a glass epoxy substrate on which a circuit pattern is formed in advance by etching or the like, and through-holes or the like are provided in positions for attaching various components (e.g., various components for signal processing such as an integrated circuit (IC) for signal processing, a resistor, and a capacitor). In addition, as already described, in the electric circuit substrate 70, in positions corresponding to the element for detection main body 40, the thermistor 60, the terminals 55a and 55b, the terminals 31a to 31c of the connector 31, and the cut-raised portion 83, attachment holes of a size according to shapes of the respective terminals are provided, and a land pattern surrounds the attachment holes. After attaching the detection element main body 40 and the thermistor 60 is completed, the electronic circuit substrate 70 to which the above-described various components are attached is mounted on the housing section 22 of the flow path forming member 20. Thereafter, an electric circuit configuration of the electronic circuit substrate 70 is completed by soldering the terminals inserted in the respective attachment holes of the electronic circuit substrate 70 to lands around them.

Figure 6:
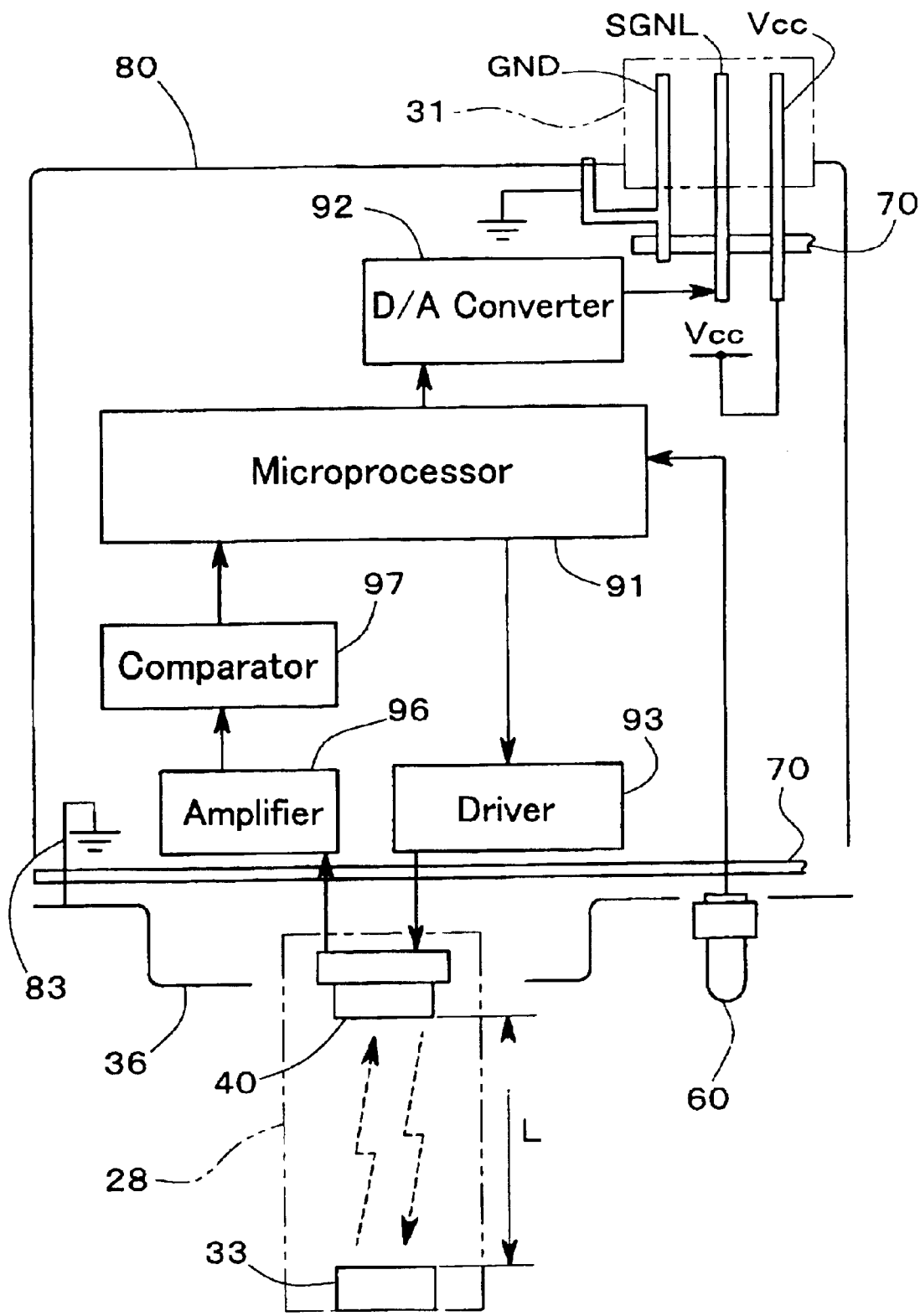
FIG. 6 is an explanatory view showing an electric structure inside the gas sensor 10.

An electric structure of the gas sensor 10 completed in this way is shown in a block diagram of FIG. 6. As shown in the figure, this electronic circuit substrate 70 includes a microprocessor 91 as a main component and also includes respective circuit elements connected to the microprocessor 91, that is, a digital/analog converter (D/A converter) 92, a driver 93, a comparator 97 to which an amplifier 96 is connected, and the like. The driver 93 and the amplifier 96 are connected to the element for detection main body 40. In addition, the thermistor 60 is directly connected to an analog input port of the microprocessor 91.

The driver 93 is a circuit for receiving an instruction from the microprocessor 91 to drive the piezoelectric element 51 of the detection element main body 40 for a predetermined time. Upon receiving an instruction from the microprocessor 91, the driver 93 outputs plural rectangular waves. Upon receiving signals of the rectangular waves output by the driver 93, the piezoelectric element 51 vibrates and functions as a transmitter to transmit an ultrasonic wave into the measurement chamber 28. Such an ultrasonic wave which is transmitted from the piezoelectric element 51 into the measurement chamber 28 as the piezoelectric element 51 vibrates upon receiving an output signal from the driver 93 is hereinafter referred to as an ultrasonic wave for detection DW.

In this embodiment, the rectangular wave output by the driver 93 is referred to herein as a "predetermined signal". It is also possible to realize the "predetermined signal" in a form other than a rectangular wave output by the driver 93.

Figure 7:
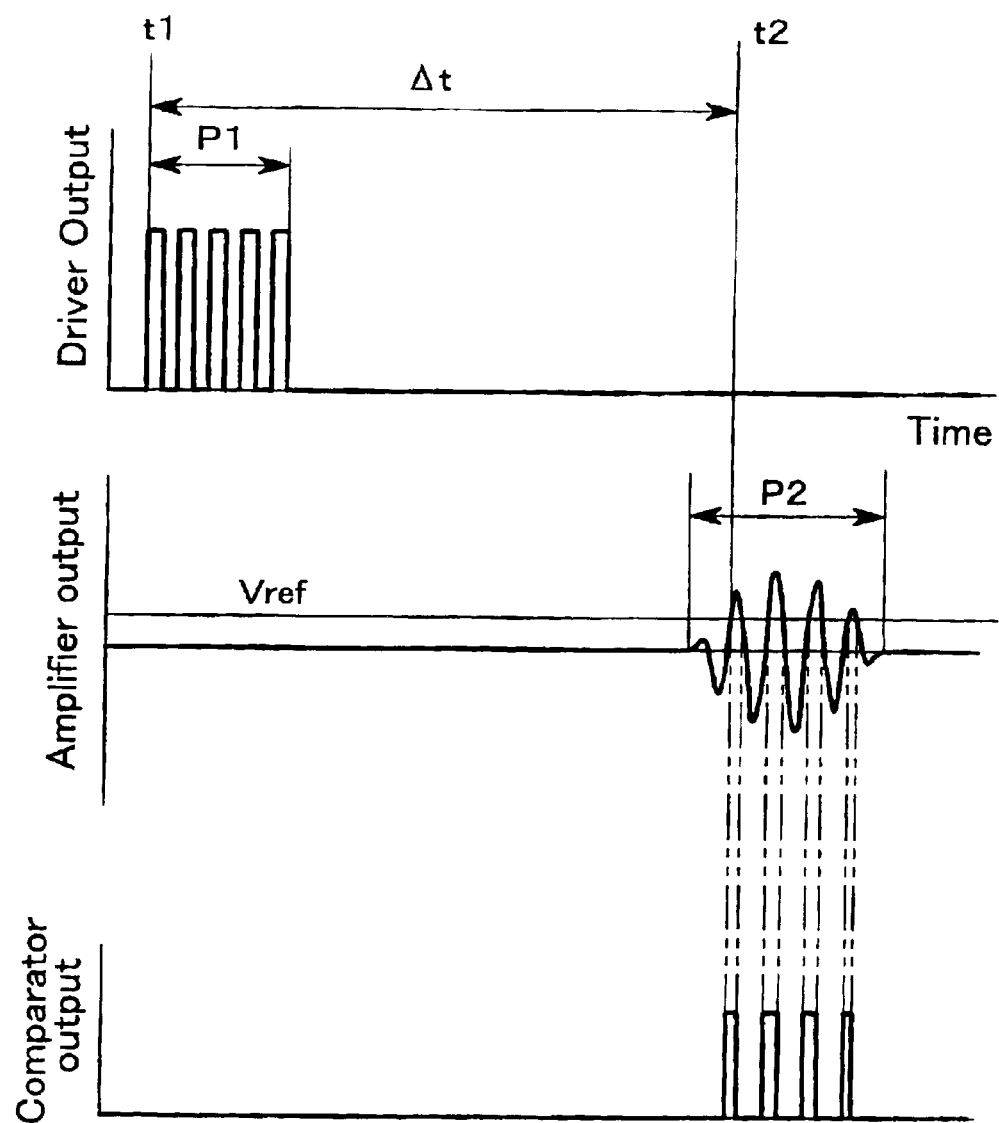
FIG. 7 is an explanatory chart illustrating a principle of detection of a gasoline vapor concentration using an ultrasonic wave.

The ultrasonic wave transmitted into the measurement chamber 28 travels straight while keeping relatively high directivity and reflects on the reflecting section 33 of the bottom portion of the measurement chamber 28 to return. When the ultrasonic wave which has returned reaches the protective film 48, vibration of the ultrasonic wave is transmitted to the piezoelectric element 51 via the protective film 48 and the acoustic matching plate 50. The piezoelectric element 51 having received the vibration of the ultrasonic wave then functions as a receiver to output an electric signal according to the vibration to the amplifier 96. This state is shown in FIG. 7. In FIG. 7, a transmission period P1 represents a period during which the piezoelectric element 51 receives the signal from the driver 93 and transmits the ultrasonic wave for detection DW (period during which the piezoelectric element 51 functions as a transmitter), and an input period P2 represents a period during which a signal of the piezoelectric element 51 having received the vibration of the ultrasonic wave is input in the amplifier 96 (period during which the piezoelectric element 51 functions as a receiver).

The signal of the piezoelectric element 51 at the time when it functions as the receiver is input in the amplifier 96 and amplified. An output of this amplifier 96 is inputted in the comparator 97 and compared here with a threshold value Vref set in advance. The threshold value Vref is set at a level in which an error signal output by the amplifier 96 due to noise can be distinguished.

In addition to those due to noise, error signals may result from reverberation or the like of the detection element main body 40 itself. Although the piezoelectric element 51 is adhered to the acoustic matching plate 50 and filled with a filler, it is capable of free end vibration to some extent and therefore may exhibit damped vibrations over a certain predetermined period even after a drive signal output from the driver 93 is turned off. In addition, a slight ultrasonic vibration propagating from the piezoelectric element 51 to its periphery, and vibration which is caused by the ultrasonic vibration reflecting on an interface of the element case 42 or the like to return may also be present. These become reverberations. An ultrasonic wave transmitted from the piezoelectric element 51 when the piezoelectric element 51 vibrates due to reverberation in the element case 42 is hereinafter referred to as a noise ultrasonic wave NW.

The comparator 97 compares the signal from the amplifier 96 with the threshold value Vref, thereby reversing its output when a magnitude of vibration received by the piezoelectric element 51 becomes equal to or larger than a predetermined magnitude. By monitoring the output of the comparator 97 with the microprocessor 91 and measuring a time Δt from output timing (timing t1 of FIG. 7) of a first ultrasonic wave from the piezoelectric element 51 until output timing (timing t2 of FIG. 7) when the output of the comparator 97 reverses, a time required for the ultrasonic wave to travel a propagation distance to and from the reflection section 33 in the measurement chamber 28 can be found. It is known that the speed C at which an ultrasonic wave propagates through a certain medium is represented by the following expression (1):

$$C = \sqrt{\frac{RT \sum C_{pn} X_n}{\sum C_{vn} X_n \sum M_n X n}} \quad (1)$$

This expression (1) is a general expression which is established for a gas in which plural components are mixed, and a variable n is a suffix indicating that the expression concerns an nth component. Therefore, Cpn represents a constant pressure specific heat of the nth component of the gas GS present in the measurement chamber 28, Cvn represents an isovolumetric specific heat of the nth component of the gas GS in the measurement chamber 28, Mn represents a molecular weight of the nth component, and Xn represents a mixture ratio of the nth component. In addition, R represents a gas constant and T represents a temperature of the gas GS in the measurement chamber 28.

The propagation speed C is defined by the temperature T and the concentration ratio Xn of the gas GS in the measurement chamber 28. The propagation speed C of an ultrasonic wave can be expressed as follows using the propagation distance L from the piezoelectric element 51 to the reflecting section 33:

$$C = 2 \times L / \Delta t \quad (2)$$

Therefore, if Δt is measured, the concentration ratio Xn, that is, a vapor concentration of gasoline can be found.

The microprocessor 91 performs an arithmetic operation in accordance with the above expression at high speed and outputs a signal corresponding to the found vapor concentration of gasoline via the D/A converter 92. This signal is output to the outside via the terminal 31b of the connector 31. In the embodiment, this signal is output to a computer, which controls a fuel injection amount of an internal combustion engine, and is used here for processing such as correcting the fuel injection amount taking into account a purge amount of gasoline from a canister.

A-5. Characteristics of the Tube Body 52

Figure 8:
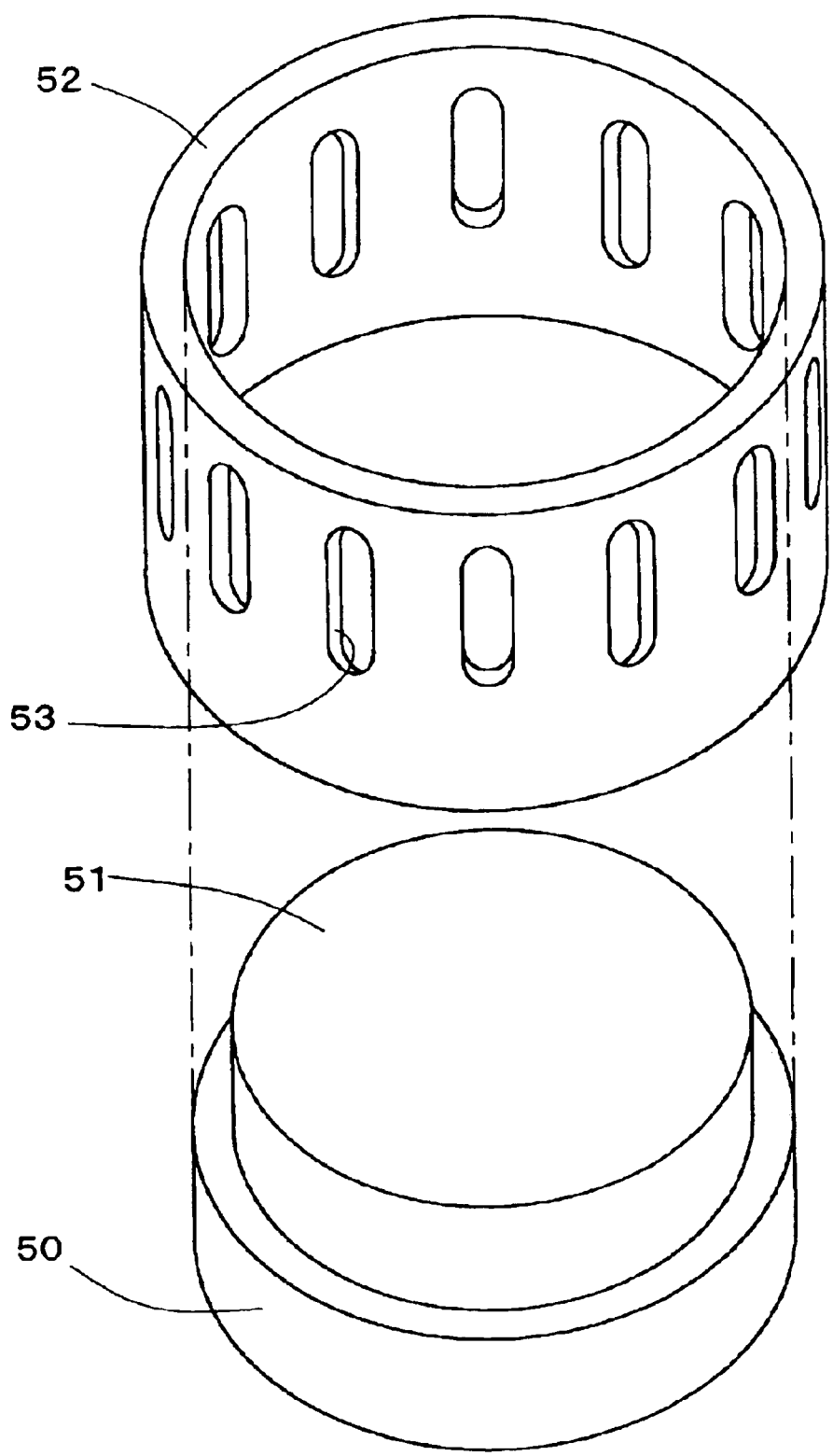
FIG. 8 is an explanatory view showing structures of an acoustic matching plate 50, a piezoelectric element 51, and a tube body 52 in a perspective shape.

Characteristics of the tube body 52 will be described with reference to FIGS. 5 and 8. FIG. 8 is a disassembled perspective view showing a relationship between the tube body 52 and the acoustic matching plate 50 and piezoelectric element 51. As shown in FIGS. 5 and 8, the tube body 52 is provided in an area between the acoustic matching plate 50 and piezoelectric element 51 and the element case 42 so as to surround the acoustic matching plate 50 and the piezoelectric element 51.

As described above, the tube body 52 is formed in a three-layer structure consisting of three types of media with different densities, namely, polyethylene terephthalate (PET) film 52a, adhesion layer 52b, and copper foil 52c. Consequently, the acoustic impedance of the tube body 52 has different values in the respective layers.

As shown in FIG. 5, the tube body 52 is formed with a polyethylene terephthalate film 52a on its outer side (element case 42 side shown in FIG. 5) and the copper foil 52c having a larger density than the polyethylene terephthalate film 52a on its inner side (piezoelectric element 51 side shown in FIG. 5). In this way, the copper foil 52c which is a medium having a larger density than urethane resin serving as a filler is used on the inner side of the tube body 52.

As shown in FIGS. 5 and 8, since an inner diameter of this tube body 52 substantially coincides with an outer diameter of the acoustic matching plate 50, the tube body 52 is closely attached to the external periphery of the acoustic matching plate 50 in a state in which it is mounted on the protective film 48. As a result, the tube body 52 is arranged in a position closer to the acoustic matching plate 50 and piezoelectric element 51 than the element case 42 in an area between the acoustic matching plate 50 and piezoelectric element 51 and the element case 42 in a state in which it is close to the acoustic matching plate 50 and piezoelectric element 51. Note that the tube body 52 and the acoustic matching plate 50 are not adhered to each other. In addition, the copper foil 52c on the inner side of the tube body 52 is not adhered to the filled layer 99.

In addition, as shown in FIGS. 5 and 8, the external diameter of the piezoelectric element 51 is made smaller than the external diameter of the acoustic matching plate 50. Therefore, a gap is formed between the internal surface of the tube body 52 surrounding the acoustic matching plate 50 and the piezoelectric element 51 and the side of the piezoelectric element 51.

As shown in FIG. 8, twelve openings 53 are provided in the tube body 52. These openings 53 are provided in positions offset upward along the axial direction of the piezoelectric element 51 (in other words, in a position offset to a side opposite the measurement chamber 28). Therefore, after assembly, the openings 53 of the tube body 52 are present in positions corresponding to the external periphery of the piezoelectric element 51 rather than the external periphery of the acoustic matching plate 50. Note that, in FIG. 8, for convenience of understanding, respective layers 52a, 52b, and 52c forming the tube body 52 are drawn integrally.

A-6. Actions and Effects of the First Embodiment

In the gas sensor 10 of the first embodiment described above, the acoustic matching plate 50 and the piezoelectric element 51 are adhered and fixed in the element case 42 to which the protective film 48 is adhered in an opening portion of its bottom surface, and the tube body 52 is provided so as to surround the acoustic matching plate 50 and the piezoelectric element 51. By providing the tube body 52 in this manner, in the case in which reverberation is generated in the filled layer 99 of the element case 42 following transmission of the ultrasonic wave for detection DW, this reverberation decreases promptly and the time during which the reverberation continues is reduced. In this way, since the time during which the reverberation continues is reduced, an acoustic level of the noise ultrasonic NW transmitted from the piezoelectric element 51 is reduced promptly.

That is, when the piezoelectric element 51 and the acoustic matching plate 50 vibrate, the noise ultrasonic wave NW is emitted in a direction other than a regular direction (measurement chamber 28 side) from the piezoelectric element 51 and the acoustic matching plate 50. Of this noise ultrasonic wave NW, noise ultrasonic wave NWs emitted in an internal peripheral surface direction of the element case 42 (horizontal direction in FIG. 5) are divided into a component NWs1 reflected on an interface with the copper foil 52c of the tube body 52 and a component NWs2 transmitting through the copper foil 52c. In addition, the component NWs2 which transmits through the copper foil 52c is further divided into a component NWs3 which reflects on an interface with the adhesion layer 52b and a component NWs4 transmitting through the adhesion layer 52b. In this way, since the noise ultrasonic wave NWs collide with the tube body 52 to be dispersed in terms of time and energy, the energy of the noise ultrasonic wave NWs returning to the piezoelectric element 51 is attenuated. As a result, an acoustic level of the noise ultrasonic wave NWs becomes low compared with the case without the tube body 52. Note that it has become clear according to results of experiments described below that duration of reverberation is reduced in the case in which the tube body 52 is provided.

Figure 9:
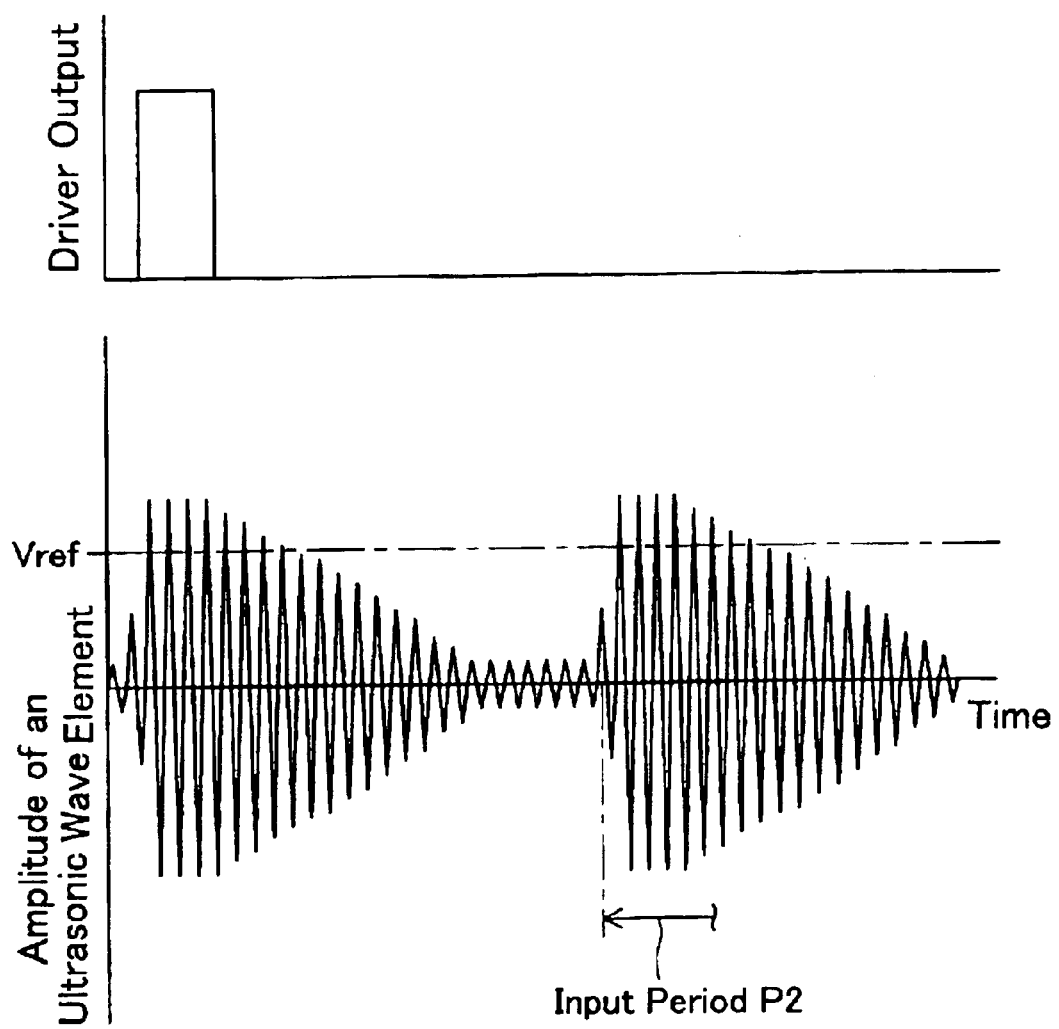
FIG. 9 is an explanatory chart showing a state in which an acoustic level of a noise ultrasonic wave NW is reduced in the gas sensor 10.

A state in which the acoustic level of the noise ultrasonic wave NW is reduced in the gas sensor 10 of the first embodiment is shown in FIG. 9. FIG. 9 is a graph showing temporal transition of a vibration state of the piezoelectric element 51 after the piezoelectric element 51 has transmitted the ultrasonic wave for detection DW upon receiving an output signal from the driver 93 (after elapse of the transmission period P1 in FIG. 7). In this graph, the horizontal axis shows an elapsed time and the vertical axis shows an amplitude of the piezoelectric element 51. This amplitude of the piezoelectric element 51 shows an amplitude detected in a vibration detector connected to the piezoelectric element 51. In this graph, a value of "Vref" of the amplitude of the piezoelectric element 51 indicates an amplitude to be detected in the case in which the piezoelectric element 51 is in a vibration state equivalent to a threshold value Vref. Note that an input period P2 indicates a period during which the piezoelectric element 51 functions as a receiver.

As shown in FIG. 9, the amplitude of the piezoelectric element 51 promptly attenuates after it is generated as the piezoelectric element 51 is vibrated by the driver 93. That is, the amplitude of the piezoelectric element 51 becomes smaller than "Vref" after the transmission of the ultrasonic wave for detection DW and becomes feeble before a beginning of the input period P2. This means that reverberation in the element case 42 is promptly reduced after the transmission of the ultrasonic wave for detection DW. Consequently, in the input period P2, the noise ultrasonic wave NW transmitted from the piezoelectric element 51 is brought into a state in which it is extremely feeble, and the piezoelectric element 51 receives the ultrasonic wave for detection DW reflected by the reflecting section 33 in this state. If the noise ultrasonic wave NW is feeble in this way, even in the case in which it interferes with the ultrasonic wave for detection DW as a reflected wave, since the degree of interference is weak, a waveform or a phase of the ultrasonic wave for detection DW is never disturbed significantly. Therefore, it becomes possible to accurately obtain an elapsed time since a first ultrasonic wave for detection DW is transmitted until it returns to the piezoelectric element 51. In addition, a signal of a level equal to or higher than the threshold value Vref can be input in the comparator 97 surely as the piezoelectric element 51 receives the ultrasonic wave DW which has returned.

In this manner, according to the gas sensor 10 of the first embodiment, it becomes possible to promptly reduce the acoustic level of the noise ultrasonic wave NW transmitted from the piezoelectric element 51, and accurate detection of a concentration of gasoline vapor based upon the ultrasonic wave for detection DW can be secured.

In addition, in the gas sensor 10 of the first embodiment, the copper foil 52c on the inner side of the tube body 52 is brought into a state in which it is not adhered to the filled layer 99 in the element case 42. In this way, the surface of the copper foil 52c slides against the filled layer 99, whereby thermal stress applied to the periphery of the acoustic matching plate 50 and the piezoelectric element 51 is eased. In addition, since the copper foil 52c and the filled layer 99 are not adhered to each other, there is a loss of ultrasonic wave energy of a reverberation at that interface. Therefore, the duration of the reverberation can be further reduced.

Figure 10:
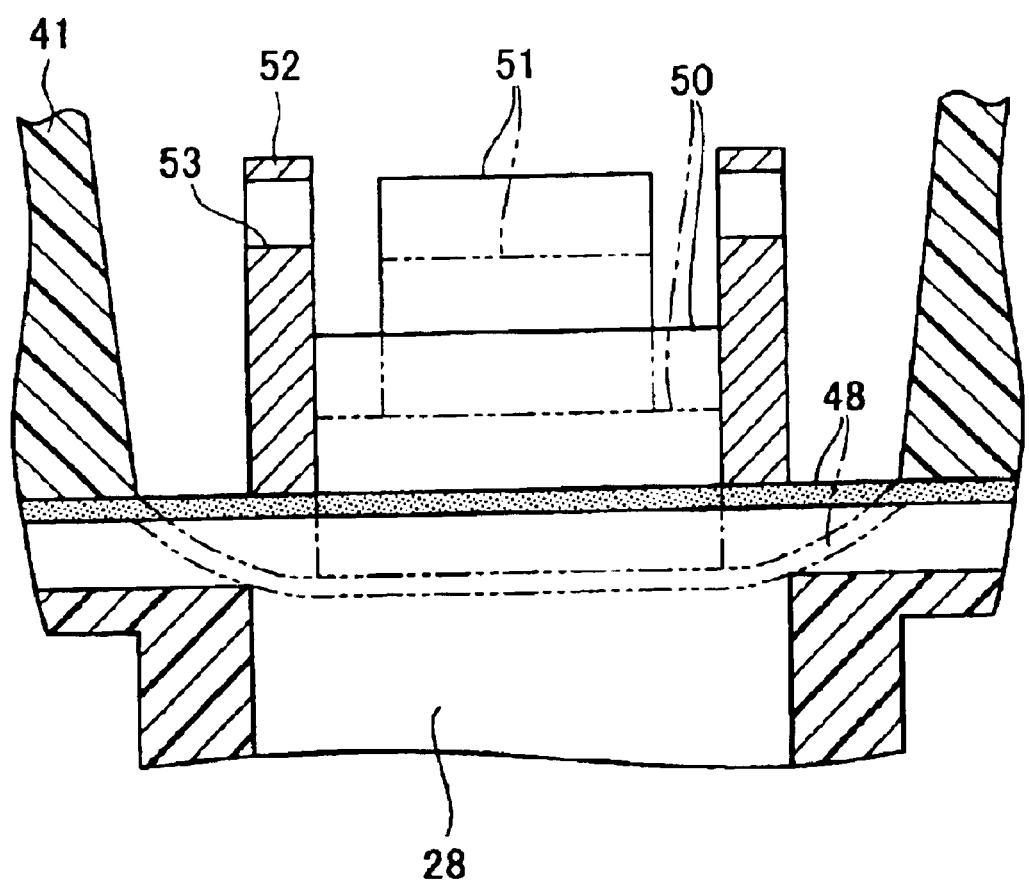
FIG. 10 is an explanatory view showing movement of the acoustic matching plate 50 and the piezoelectric element 51 to be prevented by the gas sensor 10 of this embodiment.

Moreover, in the gas sensor 10 of the first embodiment, after arranging the tube body 52 on the protective film 48 in the bottom of the element case 42 to be close to the acoustic matching plate 50 and the piezoelectric element 51, a filler is filled in the element case 42 to form the filled layer 99. A large number of openings 53 are provided in this tube body 52, and the filler penetrates into the openings 53 at the time when the filler is filled. Therefore, when the filler is hardened, the tube body 52 and the inner side portion thereof are bonded with the outer side portion of the tube body 52. Consequently, when the gas sensor 10 is exposed in a high temperature atmosphere and the filled layer 99 thermally expands, the acoustic matching plate 50 and the piezoelectric element 51 arranged in the inner side portion of the tube body 52 are prevented from moving in a direction toward the measurement chamber 28 following this thermal expansion (a state indicated by an alternate long and two short dashes line in FIG. 10). As a result, accuracy of detection for a concentration of gasoline vapor can be further improved.

In addition, in the gas sensor 10 of the first embodiment, the openings 53 provided in the tube body 52 are formed in a position offset upward along an axial direction of the piezoelectric element 51. Consequently, positional movement of the acoustic matching plate 50 and the piezoelectric element 51 following the thermal expansion of the filled layer 99 is suppressed and, at the same time, appropriate slip of the surface of the copper foil 52c against the filled layer 99 is secured, and thermal stress applied to the periphery of the acoustic matching plate 50 and the piezoelectric element 51 is eased. Therefore, reduction of the duration of reverberation can be realized while securing accuracy of detection of gasoline vapor concentration.

Although the tube body 52 is formed using three types of media in the first embodiment, the tube body may be formed of only one type of material. As a material in this case, a material with a quality different from urethane resin serving as the filled layer (e.g., a metal such as copper) can be used. In this manner, the noise ultrasonic wave NWs emitted in the internal peripheral surface direction of the element case 42 transmits through the tube body or collides with the tube body to be reflected, whereby its energy is attenuated. Therefore, the duration of the reverberation in the filled layer 99 can be reduced compared with the case without the tube body.

In addition, although the tube body 52 is formed in a shape surrounding the entire periphery of the acoustic matching plate 50 and the piezoelectric element 51 in the first embodiment, it is also possible to adopt a structure in which the tube body 52 is constituted from plural members and the respective members are arranged around the acoustic matching plate 50 and the piezoelectric element 51. In this structure, the members constituting the tube body 52 may be arranged with gaps among the members. In this way, a state in which the filler has flown in the gaps provided among the members is obtained, and in the case in which the filled layer 99 expands, movements of the respective members constituting the tube body 52 are restricted by the expanded filler. Therefore, as in the case in which the opening 53 is provided in the above-mentioned embodiment, the acoustic matching plate 50 and the piezoelectric element 51 can be prevented from moving in a direction toward the measurement chamber 28.

In the first embodiment, the filled layer 99 in the element case 42 only has to be formed with a height at which the piezoelectric element 51 is embedded. For example, it is also possible to adopt a structure in which the filled layer 99 is provided with a height at which the top end of the tube body 52 is not embedded and the lead wires 54a and 54b of the piezoelectric element 51 are connected to the terminals 55a and 55b via the copper foil 52c at the top end of the tube body 52.

A-7. Results of Experiments

The above description "by providing the tube body 52 so as to surround the acoustic matching plate 50 and the piezoelectric element 51, the reverberation generated in the element case 42 following the transmission of the ultrasonic wave for detection DW attenuates promptly, and time during which the reverberation continues is reduced" will be indicated below based upon an experiment 1. Conditions of this experiment 1 are shown in FIG. 11.

Figure 11:
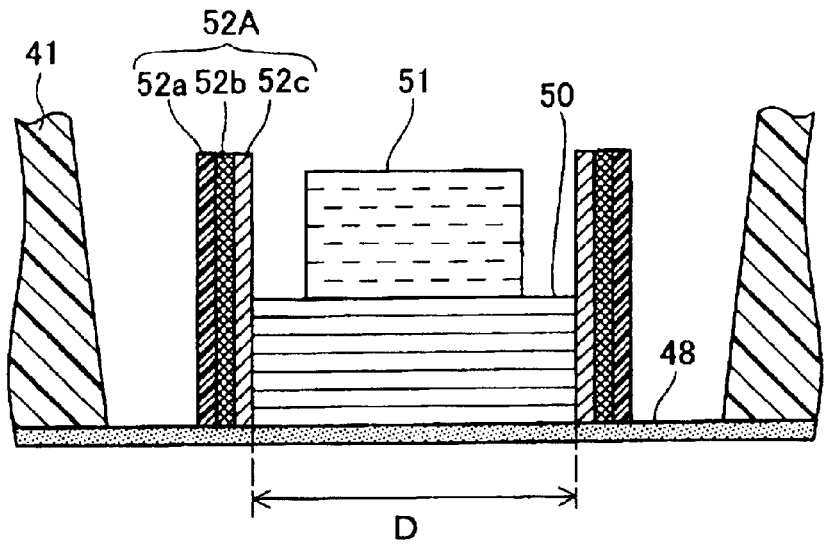
FIGS. 11(A) and 11(D) are explanatory views showing conditions of an experiment 1 concerning a first embodiment.
Figure 11:
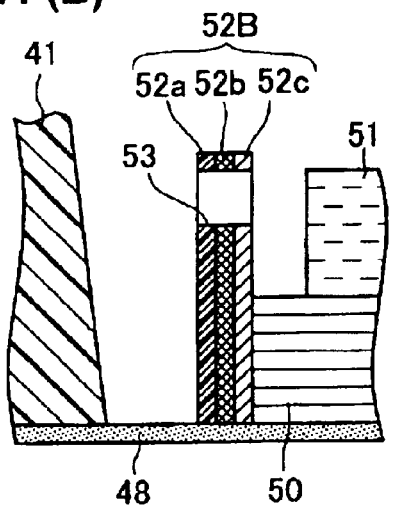
Figure 11:
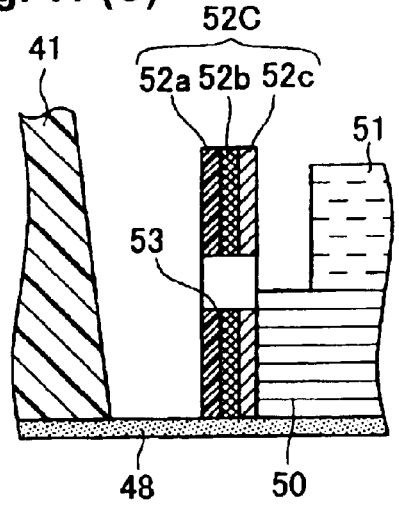
Figure 11:
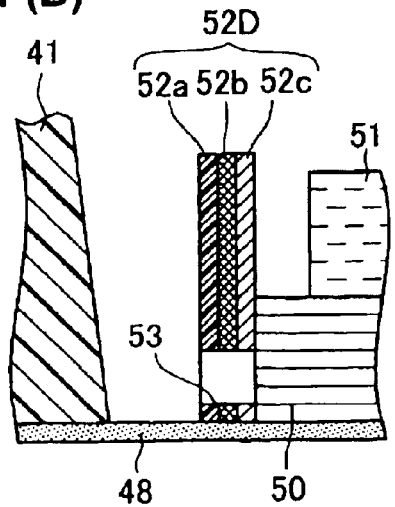

First, one element case in which the tube body 52 was not provided around the acoustic matching plate 50 and the piezoelectric element 51 was prepared and, at the same time, four types of element cases in which one of tube bodies 52A to 52D was provided around the acoustic matching plate 50 and the piezoelectric element 51 were prepared as shown in FIG. 11. In these four types of element cases, the tube body 52A without the opening 53, the tube body 52B in which the opening 53 was formed in its upper part, the tube body 52D in which the opening 53 was formed in its lower part, and the tube body 52C in which the opening 53 was formed between the upper part and the lower part (hereinafter referred to as central part) are housed. Concerning a material of the tube bodies 52A to 52D, a direction and an inner diameter D of the copper foil 52c, conditions were the same as those in the above-described embodiment. Note that, in FIG. 11, descriptions of the filled layer 99 and the like formed in the element case are omitted for convenience of description.

For such five types of element cases, the long time required to reduce reverberation in the element case 42 to a fixed level or less after the ultrasonic wave for detection DW was transmitted was measured plural times under a high temperature condition of 85° C. An average value of the plural times of measurement is shown in FIG. 12(A) as a result of the experiment 1. As shown in FIG. 12(A), the time during which the reverberation continued was shorter in the element cases which were provided with the tube bodies 52A to 52D as compared with the element case which was not provided with the tube body 52. In addition, concerning the four types of element cases which were provided with the tube bodies 52A to 52D, the time during which the reverberation continued was shorter in the order of the element case including the tube body 52D, the element case including the tube body 52C, the element case including the tube body 52A, and the element case including the tube body 52B. According to this result, it is surmised that an effect for reducing the duration of a reverberation becomes high in the case in which the opening 53 of the tube body is placed in an upper position.

Next, an experiment 2 will be described. In experiment 2, concerning the element case including the tube body 52B in which time during which a reverberation continued was shortest, the tube body 52B was changed to a tube body 52E described below, and the duration of a reverberation was measured with the same method as in experiment 1. The tube body 52E was a tube body in which directions of the polyethylene terephthalate film 52a and the copper foil 52c were opposite the direction of the tube body 52B (i.e., the polyethylene terephthalate film 52a was on the inner side (piezoelectric element 51 side shown in FIG. 5) and the copper foil 52c was on the outer side (element case 42 side shown in FIG. 5)). Also, the position of the opening 53, a material and an inner diameter D of the tube body 52E were the same as those of the tube body 52B. The result of this experiment 2 is shown in FIG. 12(B). As shown in FIG. 12(B), a duration of a reverberation in the element case including the tube body 52E was shorter than that in the element case which was not provided with the tube body 52 and was longer than that in the element case including the tube body 52B.

Next, an experiment 3 will be described. In experiment 3, concerning the element case including the tube body 52B having the shortest reverberation time, the tube body 52B was changed to a tube body 52F or 52G described below, and the duration of a reverberation was measured as in experiment 1. The tube bodies 52F and 52G were tube bodies in which inner diameters D thereof were made larger than that of the tube body 52B, the inner diameter D of the tube body 52F was "φ 12.7" and the inner diameter D of the tube body 52G was "φ 14.5". In the tube bodies 52F and 52G, the position of the opening 53, the orientation of the copper foil 52c, and the material of the tube body 52 were the same as those of tube body 52B. The result of experiment 3 is shown in FIG. 12(C). As shown in FIG. 12(C), a duration of reverberation in each element case including the tube body 52F or 52G was shorter than that of the element case which was not provided with the tube body 52 and longer than that of the element case including the tube body 52B. Also, the time during which the reverberation continued was shorter in the order of the element case including the tube body 52F and the element case including the tube body 52G. According to this result, it is surmised that the duration of the reverberation becomes shorter as the inner diameter of the tube body becomes smaller and the distance from the tube body to the acoustic matching plate 50 and the piezoelectric element 51 becomes shorter.

Next, an experiment 4 will be described. In experiment 4, concerning the element case including the tube body 52B having the shortest reverberation time, the material of the tube body 52B was changed to a tube body 52H or 52I described below, and the duration of a reverberation was measured as in experiment 1. The tube body 52H was formed in a three-layer structure consisting of the polyethylene terephthalate film 52a, the adhesion layer 52B, and aluminum, and the tube body 52I was a tube body in which the copper foil 52c was adhered between two polyethylene terephthalate films. In the tube bodies 52H and 52I, the position of the opening 53, and the direction and the inner diameter D of the metal layer (aluminum) were the same as those of the tube body 52B. The result of experiment 4 is shown in FIG. 12(D). As shown in FIG. 12(D), the duration of the reverberation in each element case including the tube body 52H or 52I was shorter than that of the element case which was not provided with the tube body 52 and longer than that of the element case including the tube body 52B. Also, the time during which the reverberation continued was shorter in the order of the element case including the tube body 52H and the element case including the tube body 52I. According to this result, it is surmised that, when densities of media of an internal surface and an external surface of a tube body are varied, a difference is generated in acoustic impedance between the internal surface and the external surface of the tube body to reduce the duration of the reverberation.

B. Second Embodiment

Figure 13:
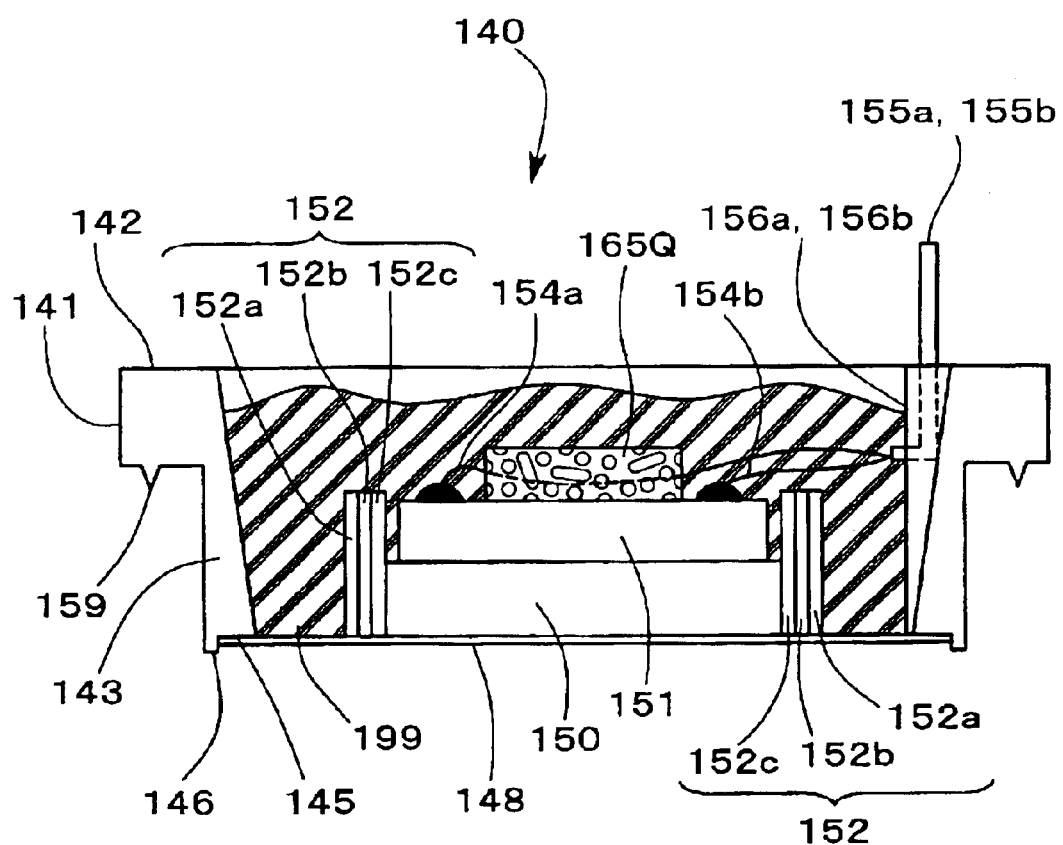
FIG. 13 is an explanatory view showing a sectional structure of a detection element main body 140 provided in a gas sensor of a second embodiment of the present invention.

Next, a second embodiment of the present invention will be described. A gas sensor of the second embodiment is different from the gas sensor of the first embodiment in that a plate-like body 165Q, which is formed using a porous body, is provided in the element case 42 of the element for detection main body 40. A sectional structure of an element for detection main body 140 provided with the plate-like body 165Q in an element case 142 in this way is shown in FIG. 13. FIG. 13 represents a section corresponding to FIG. 5. In FIG. 13, concerning the respective portions common to the detection element main body 40 in the first embodiment, numerals of second and first positions and alphabets following them of symbols are represented using the same numerals or alphabets as those in FIG. 5. A tube body 152 is the same as the above-mentioned tube body 52 and is arranged in the same position as the tube body 52.

As shown in FIG. 13, the plate-like body 165Q made of foamed silicon is provided on a surface (hereinafter referred to as an upper surface) of a piezoelectric element 151 opposed to a surface of a filled layer 199. In this embodiment, the above-mentioned plate-like body 165Q is referred to herein as the "surface member".

Figure 14:
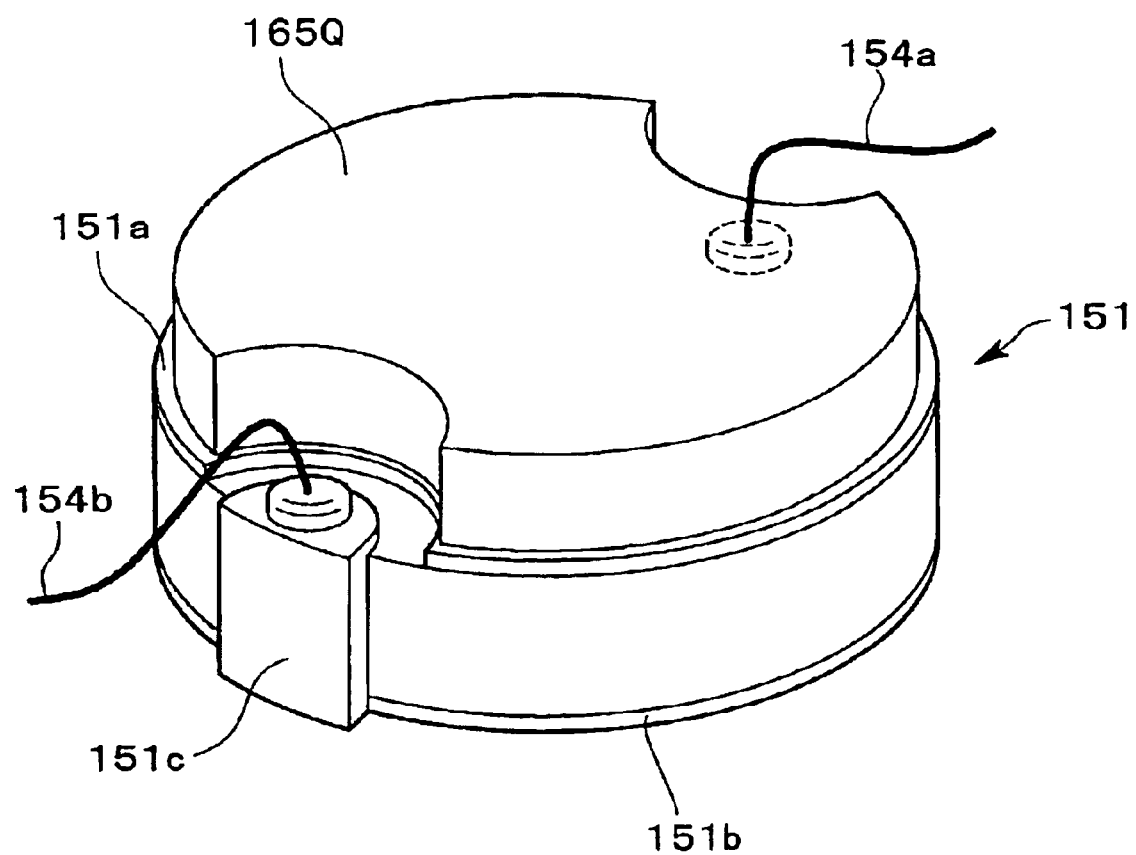
FIG. 14 is an explanatory view showing a perspective shape in the vicinity of an upper surface of a piezoelectric element 151.

A perspective shape in the vicinity of the upper surface of the piezoelectric element 151 is shown in FIG. 14. As shown in FIG. 14, a positive electrode 151a and a negative electrode 151b are formed by evaporation on the upper surface and the lower surface of the piezoelectric element 151, respectively. The negative electrode 151b has a folded-back portion 151c which is a portion for inputting and outputting from the negative electrode 151b. This folded-back portion 151c is folded back to the upper surface of the piezoelectric element 151 so as not to contact the positive electrode 151a. One end of each of the lead wires 154a and 154b is soldered to the positive electrode 151a and the folded-back portion 151c of the negative electrode 151b, respectively. The plate-like body 165Q is adhered to an area excluding the portion, where the lead wire 154a is soldered, on the positive electrode 151a and fixed to the piezoelectric element 151.

In this embodiment, a silicon adhesive which is capable of adhering the plate-like body 165Q to the positive electrode 151a of the piezoelectric element 151 without a gap is used as an adhesive for the plate-like body 165Q. It is also possible to use an adhesive material (e.g., a couple-face tape) other than the silicon adhesive. In the case in which a couple-face tape is used, reduction of hardening time of an adhesive and reduction of working man-hours required for adhesion can be realized.

According to the gas sensor of the second embodiment constituted as described above, in the case in which a reverberation is generated in the filled layer 199 of the element case 142 following transmission of an ultrasonic wave for detection DW, this reverberation decreased promptly due to actions of the tube body 152 and the plate-like body 165Q, and time during which the reverberation continues is further shortened. In this way, since the time during which the reverberation continues is further shortened, an acoustic level of a noise ultrasonic wave NW transmitted from the piezoelectric element 151 is reduced more promptly.

That is, an energy of a noise ultrasonic wave NWs emitted in the internal peripheral surface direction of the element case 142 (horizontal direction in FIG. 13) by vibration of the piezoelectric element 151 and the acoustic matching plate 150 is attenuated by collision of the noise ultrasonic wave NWs with the tube body 52 as in the first embodiment. In addition, a noise ultrasonic wave NWu emitted in the surface direction of the filled layer 199 (upward direction in FIG. 13) from the positive electrode 151a side of the piezoelectric element 151 by the vibration of the piezoelectric element 151 and the acoustic matching plate 150 is divided into a component NWu1 to be reflected on an interface with the hardened silicon adhesive and a component NWu2 transmitting through the hardened silicon adhesive. Further, the component NWu2 transmitted through the silicon adhesive is further divided into a component NWu3 to be reflected on the interface with the plate-like body 165Q and the component NWu4 transmitting through the plate-like body 165Q. In this way, the noise ultrasonic wave NWu collides with the hardened silicon adhesive or the plate-like body 165Q to be dispersed in terms of time and energy, and the energy of the noise ultrasonic wave NWu returning to the piezoelectric element 151 is attenuated. As a result, an acoustic level of the noise ultrasonic wave NWu is reduced compared with the case without the plate-like body 165Q.

Moreover, the above-mentioned components NWu3 and NWu4 collide with a surface of the porous body and a surface of an inner wall forming foams inside the porous body, respectively. Therefore, the degree of the noise ultrasonic wave NWu colliding with the plate-like body 165Q increases, and an attenuation efficiency of the energy of the noise ultrasonic wave NW increases. Thus, a gas sensor with a short duration of reverberation time can be realized.

In addition, according to the gas sensor of the second embodiment, the plate-like body 165Q is adhered and fixed to the upper surface of the piezoelectric element 151. Consequently, in the case in which a temperature around a part where the gas sensor is set (hereinafter referred to as ambient temperature) rises, even if a force following expansion of the filled layer 199 acts on the plate-like body 165Q such that the plate-like body 165Q separates from the upper surface of the piezoelectric element 151, since the plate-like body 165Q stays on the upper surface of the piezoelectric element 151 against such a force, a situation in which foams are generated between the piezoelectric element 151 and the plate-like body 165Q is less likely to occur. As a result of foams becoming less likely to be generated in this manner, a situation in which duration of the reverberation and sensitivity of the piezoelectric element 151 changes largely with the piezoelectric element 151 subjected to a local stress by the foams is avoided, and characteristic change of the gas sensor following an increase in ambient temperature is suppressed. Therefore, accurate detection of a gasoline vapor concentration can be realized regardless of the change in the ambient temperature.

Figure 15:
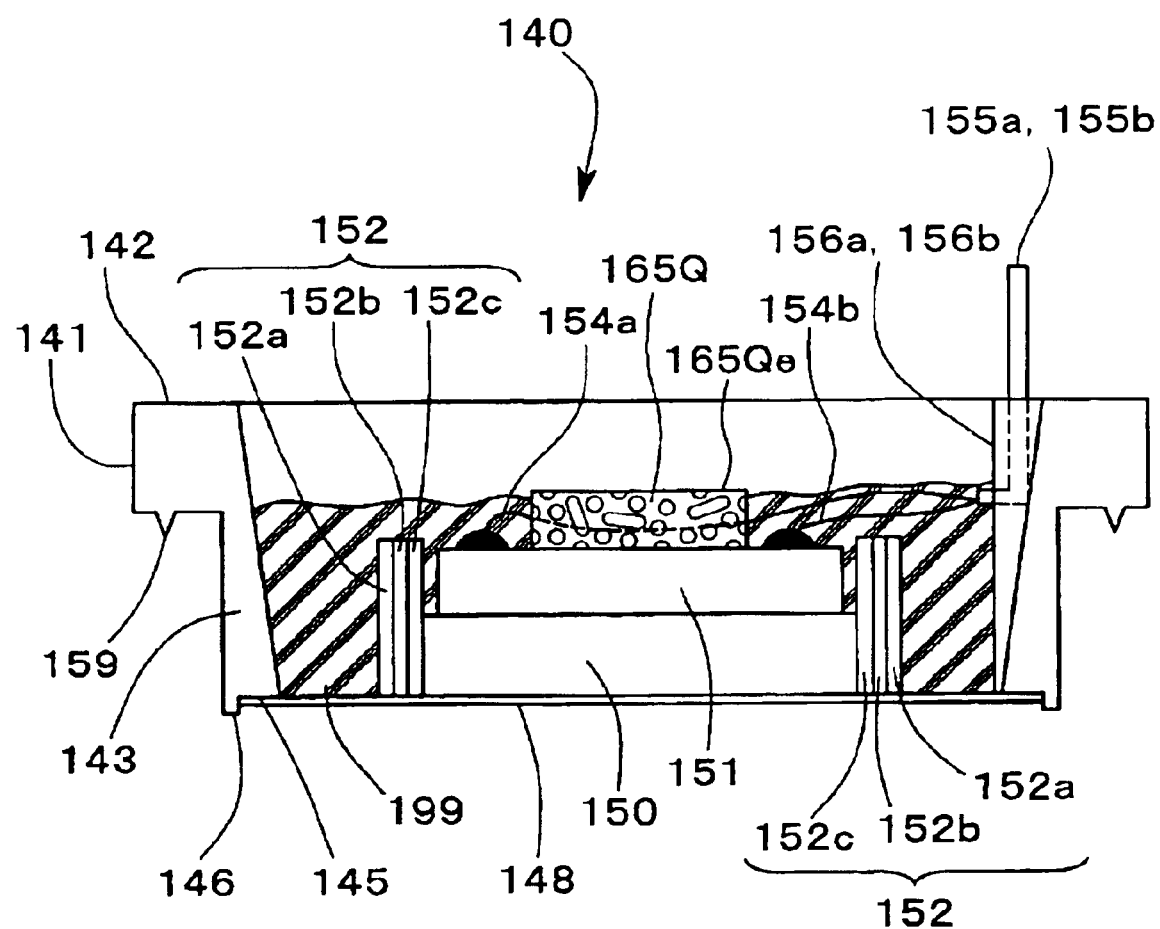
FIG. 15 is an explanatory view showing a modified example of the second embodiment.

In the above-mentioned second embodiment, the filled layer 199 in the element case 142 only has to be formed with a height at which the piezoelectric element 151 is embedded. For example, as shown in FIG. 15 representing a modified example of the second embodiment, a structure may be adopted in which a surface 165Qe on the opposite side of the piezoelectric element 151 of the plate-like body 165Q is not embedded in the filled layer 199, and a part of the plate-like body 165Q including the surface 165Qe is exposed above the surface of the filled layer 199.

C Third Embodiment

Figure 16:
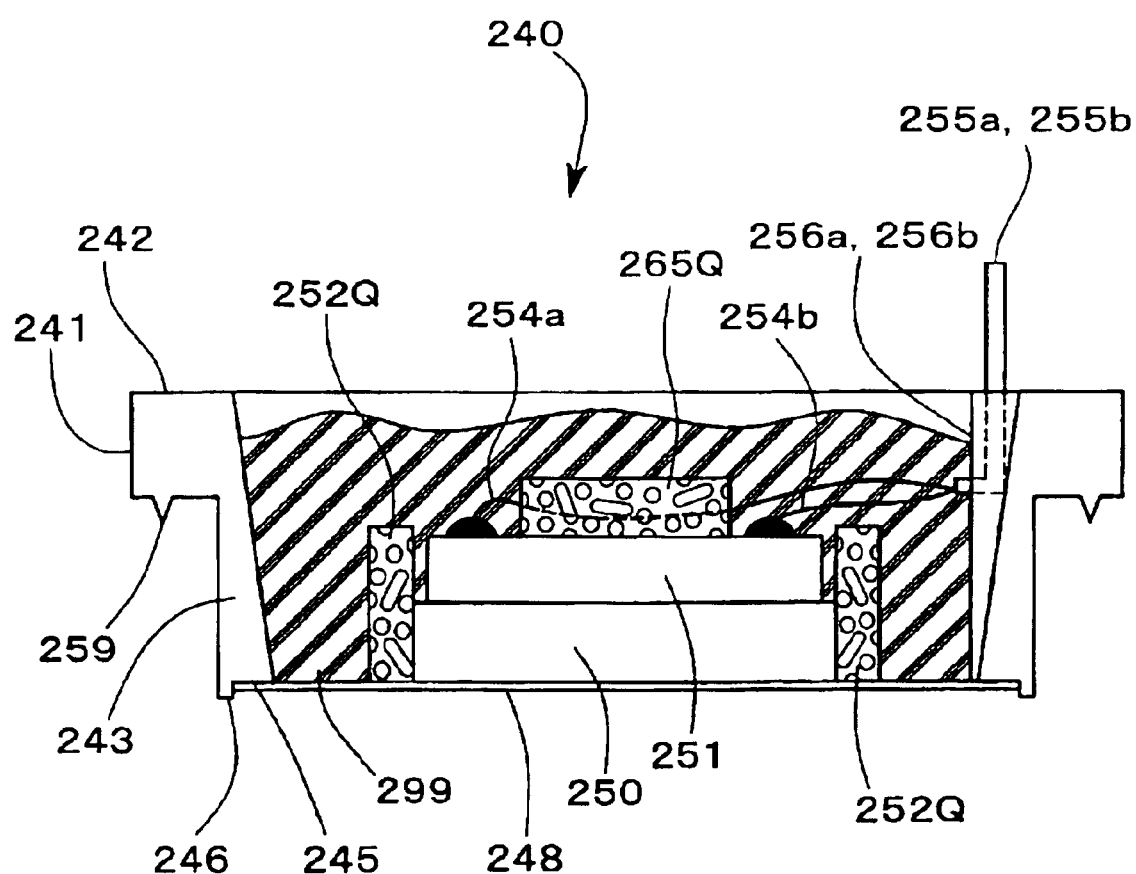
FIG. 16 is an explanatory view showing a sectional structure of an element for detection main body 240 provided in a gas sensor of a third embodiment of the present invention.

Next, a third embodiment of the present invention will be described. A gas sensor of the third embodiment is different from the gas sensor of the second embodiment in that the tube body 152 provided in the element case 142 is formed using a porous body. A section of such an element for detection main body 240 is shown in FIG. 16. FIG. 16 shows a section corresponding to FIG. 13. In FIG. 16, concerning the respective portions common to the element for detection main body 140 in the second embodiment, numerals of second and first positions and alphabets following them of symbols are represented using the same numerals or alphabets as those in FIG. 13. A plate-like body 265Q is the same as the above-mentioned plate-like body 165Q and arranged in the same position as the plate-like body 165Q.

As shown in FIG. 16, a tube body 252Q made of foamed silicon is provided in an area between the acoustic matching plate 250 to the piezoelectric element 251 and the element case 242 so as to surround the acoustic matching plate 250 and the piezoelectric element 251. In this embodiment, the above-mentioned tube body 252Q is an "intervening member".

According to the gas sensor of the third embodiment constituted as described above, since the noise ultrasonic wave NWs collides with a surface of the porous body and a surface of an inner wall forming foams inside the porous body, a degree of the noise ultrasonic wave NWs colliding with the tube body 252Q increases. Therefore, the time during which the reverberation continues can be shortened to the same degree as the second embodiment (the case in which a tube body is formed in a three-layer structure consisting of PET, an adhesive layer, and a copper foil).

In the third embodiment, the filled layer 299 in the element case 242 only has to be formed with a height at which the piezoelectric element 251 is embedded, and it is allowable to change a state of embedding the plate-like body 265Q by the filled layer 299 to the same state as shown in FIG. 15.

As the porous body to be used in formation of the plate-like body 165Q or 265Q or the tube body 252Q in the second and third embodiments, foamed urethane, foamed rubber, porous ceramics, porous carbon, and the like can be used in addition to foamed silicon.

In addition, in the second and third embodiments, at least a part of the plate-like body 165Q or 265Q or the tube body 252Q is embedded in the filled layer 199 or 299. In such an embedded part, since urethane as a filler penetrates into the porous body, the amount of air remaining in the porous body is reduced. When the filler is filled in foams in this way, since a reflected component of the noise ultrasonic wave NW in the foam portion decreases, the noise ultrasonic wave NW reflected in the direction of the piezoelectric element 151 or 251 decreases, and the duration of the reverberation can be further suppressed. In addition, since the air volume in the porous body decreases, in the case in which the filled layer 199 or 299 expands following increase in an ambient temperature, the piezoelectric element 151 or 251 becomes less susceptible to local stress according to the increase in the volume of air in the porous body. Therefore, a change in the sensitivity of the piezoelectric element 151 or 251 following an increase in ambient temperature can be suppressed.

Figure 17:
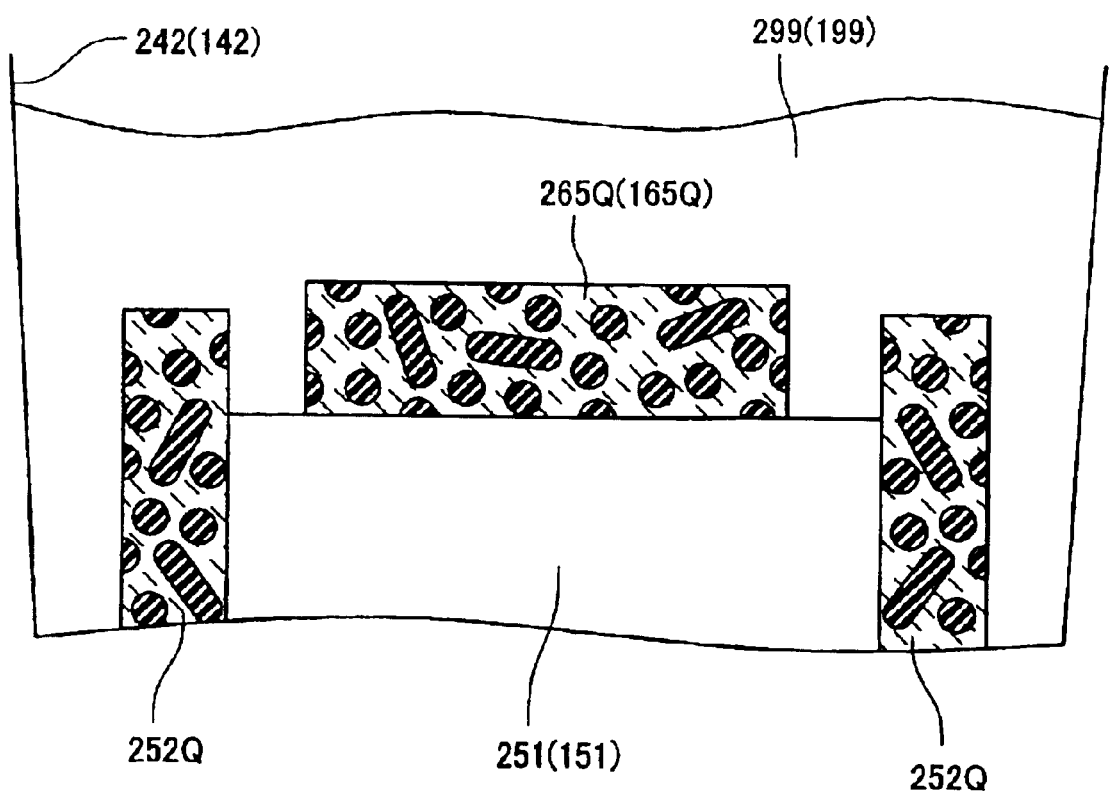
FIG. 17 is an explanatory view showing, in a section, a state in which urethane as a filler penetrates into foams present inside a porous body.

In addition, as shown in FIG. 17, if a structure is adopted in which urethane as a filler penetrates into foams existing inside the porous body, a state is obtained in which almost no air exists in the porous body embedded in the filled layer 199 or 299. Therefore, the characteristic change of the gas sensor following an increase in ambient temperature can be suppressed totally. Such a structure can be realized by defoaming the porous body under vacuum after filling urethane, forming the plate-like body 165Q or 265Q or the tube body 252Q with a porous body having continuous foams, or the like.

E. Results of Experiments;

It is also clarified by experimental data as shown below that the gas sensors of the second and third embodiments realize the above-mentioned operational effects.

Figure 18:
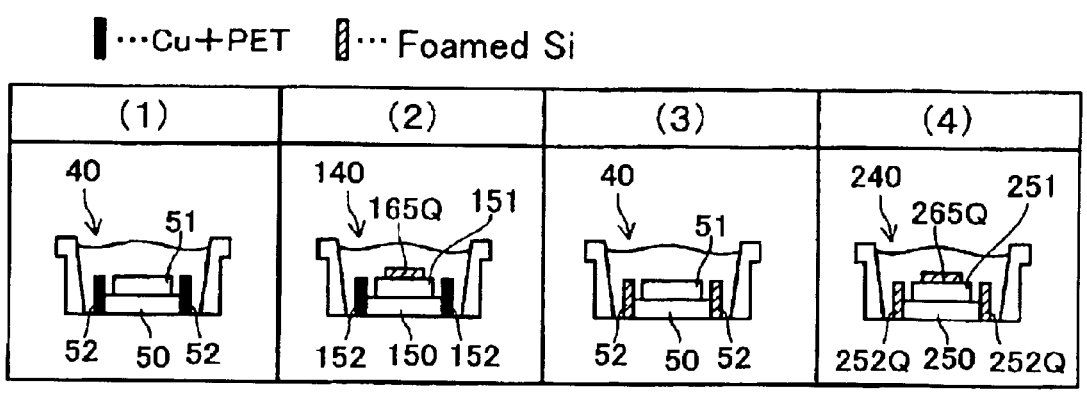
FIGS. 18(A) and 18(B) are explanatory views and a table indicating conditions and results of experiments concerning the second and third embodiments.

FIG. 18 shows explanatory views and a table indicating conditions and results concerning the second and third embodiments. FIG. 18(A) represents four types of detection element main bodies which were used for the experiment. As shown in FIG. 18(A), in this experiment, the four types of detection element main bodies of the following (1) to (4) were prepared:
  (1) the detection element main body 40 in the first embodiment (provided with the tube body 52 consisting of the three layer structure of the PET film, the adhesive layer, and the copper foil);
  (2) the detection element main body 140 in the second embodiment (provided with the tube body 152 consisting of the three layer structure of the PET film, the adhesive layer, and the copper foil and the plate-like body 165Q formed of foamed silicon);
  (3) the detection element main body 40 in the first embodiment, in which the tube body 52 is formed of foamed silicon; and
  (4) the detection element main body 240 in the third embodiment (provided with the tube body 252Q formed of foamed silicon and the plate-like body 265Q formed of foamed silicon).

First, four gas sensors provided with the above-mentioned respective detection element main bodies were set in predetermined parts where the ambient temperature was 25° C. Next, the ambient temperature of the setting parts was changed to "85° C.", and the time during which a reverberation continued after the ultrasonic wave for detection DW was transmitted was measured. FIG. 18(B) shows measurement values for the duration of the reverberation obtained for the respective gas sensors in the form of a table.

The below listed facts of <a> and <b> were found from the table shown in FIG. 18(B).

<a> Even if the material of the tube body is changed to foamed silicon from the above-mentioned three layer structure, the duration of the reverberation is reduced to the same degree (comparison between the measurement values of (1) and the measurement values of (3)).
  <b> In the case in which the plate-like body 165Q or 265Q is provided in addition to the tube body, the duration of the reverberation is reduced more than the case in which only a tube body is provided (comparison between the measurement values of (1) and the measurement values of (2), and comparison between the measurement values of (3) and the measurement values of (4)).

Various embodiments of the present invention have been described above. The present invention is not limited to such embodiments, but can be applied to, for example, a temperature sensor or a specific heat sensor using an ultrasonic wave, and a sensor for detecting various characteristics of a gas with a method other than using the ultrasonic wave within a range in which the gist of the present invention is not changed.

In addition, in the above-described embodiments, a structure may be adopted in which only a plate-like body serving as a porous body is provided without providing a tube body. According to this structure, the energy of the noise ultrasonic wave NWu emitted in a surface direction of a filled layer from a piezoelectric element is attenuated by collision with the plate-like body.

Therefore, the time during which a reverberation continues can be reduced by employing the plate-like body alone. In addition, the above-described plate-like body may be formed with a material other than copper (a material having a quality different from a filler).

Although the gas sensor is constituted such that the piezoelectric element 51 is caused to function as a transmitter and a receiver of the ultrasonic wave for detection DW by providing the reflecting section 33 in the measurement chamber 28, the prompt reduction of reverberation as shown in FIG. 9 has an important meaning even in the case in which the reflecting section 33 as described above is not provided and an piezoelectric element as a transmitter (referred to as element for transmission) and an piezoelectric element as a receiver (referred to as element for reception) are provided separately. That is, after the ultrasonic wave for detection DW is transmitted from the element for transmission to the element for reception, if a reverberation in an element case housing the element for transmission is reduced promptly as shown in FIG. 9, a noise ultrasonic wave NW is prevented from being transmitted from the element for transmission after transmission of the ultrasonic wave for detection DW. For example, before the ultrasonic wave for detection DW is transmitted again from the element for transmission or when the ultrasonic wave for detection DW is transmitted again in order to again perform detection of a concentration, the strong noise ultrasonic wave NW is never transmitted to the element for reception. Therefore, a comparator 97 connected to the element for reception never outputs a signal from the element for reception having received the noise ultrasonic wave NW to the microprocessor 91 confusing it with a signal based upon the ultrasonic wave for detection DW.

This application is based on Japanese Patent Application No. 2002-60683 filed Mar. 6, 2002, incorporated herein by reference in its entirety.

What is claimed is:

1. A gas sensor including a detection element provided facing a predetermined flow path of a gas and receiving a predetermined signal causing the detection element to vibrate, and detecting means for transmitting a vibration wave having energy generated by vibration of the detection element in the flow path direction to detect characteristics of the gas, the gas sensor comprising:
  a housing for housing the detection element in a form capable of transmitting the vibration wave for detection in the flow path direction;
  an attenuation member, provided in the housing, for attenuating the energy of a vibration wave emitted in a direction different from the transmitting direction and colliding with the attenuation member; and
  a filled layer formed by introducing a filler into the housing, said filled layer embedding at least the detection element,
  wherein the attenuation member is a surface member provided on the surface of the detection element opposite the surface of the filled layer, said surface member comprising a porous body, at least a part of the porous body is embedded in the filled layer, and the filler penetrates or permeates into the porous body.

2. The gas sensor as claimed in claim 1,
  wherein the surface member is adhered and fixed to the detection element.

3. The gas sensor as claimed in claim 1, comprising a reflecting section for reflecting the vibration wave for detection, which is transmitted from one detection element in the flow path direction, to a direction of the detection element,
  said detecting means detecting characteristics of the gas based on the vibration wave for detection reflected by the reflecting section and received by said one detection element.

4. The gas sensor as claimed in claim 1, comprising a reflecting section for reflecting the vibration wave for detection, which is transmitted from one detection element in the flow path direction, to a direction of the detection element, said detecting means detecting characteristics of the gas based on the vibration wave for detection reflected by the reflecting section and received by said one detection element.

5. A gas sensor including a detection element provided facing a predetermined flow path of a gas and receiving a predetermined signal causing the detection element to vibrate, and detecting means for transmitting a vibration wave having energy generated by vibration of the detection element in the flow path direction to detect characteristics of the gas, the gas sensor comprising:

a housing for housing the detection element in a form capable of transmitting the vibration wave for detection in the flow path direction;

an attenuation member, provided in the housing, for attenuating the energy of a vibration wave emitted in a direction different from the transmitting direction and colliding with the attenuation member; and a filled layer formed by introducing a filler into the housing, said filled layer embedding at least the detection element and part of said attenuation member, wherein the attenuation member is an intervening member provided in a position surrounding the detection element between the housing and the detection element, and the intervening member comprises plural media having different densities.

6. The gas sensor as claimed in claim 5, wherein the intervening member surrounds the entire periphery of the detection element.

7. The gas sensor as claimed in claim 5, wherein the intervening member comprises a porous body.

8. The gas sensor as claimed in claim 5, wherein the intervening member is arranged in a position adjacent to the detection element.

9. The gas sensor as claimed in claim 5, wherein the intervening member comprises a medium having a density larger than that of the filler on the detection element side.

10. The gas sensor as claimed in claim 9, wherein a medium of the intervening member on the housing side comprises a synthetic resin and a medium on the detection element side comprises a metal.

11. The gas sensor as claimed in claim 10, wherein the metal serving as a medium on the detection element side is not adhered to the filled layer.

12. The gas sensor as claimed in claim 11, comprising a film which is mounted on an opening portion of the housing and which partitions the housing and the flow path, wherein a matching member, which is mounted on the film and transmits vibration of the detection element to the flow path via the film, and the detection element, which is mounted on a surface on the opposite side of a mounting surface of the matching member to the film, are housed in the housing, and the intervening member is provided in a position surrounding the detection element and the matching member from the housing to the matching member and the detection element, and the intervening member has a predetermined number of holes offset to a side opposite the flow path side of the intervening member.

13. A gas sensor including a detection element provided facing a predetermined flow path of a gas and receiving a predetermined signal causing the detection element to vibrate, and detecting means for transmitting a vibration wave having energy generated by vibration of the detection element in the flow path direction to detect characteristics of the gas, the gas sensor comprising:

a housing for housing the detection element in a form capable of transmitting the vibration wave for detection in the flow path direction;

an attenuation member, provided in the housing, for attenuating the energy of a vibration wave emitted in a direction different from the transmitting direction and colliding with the attenuation member; and a filled layer formed by introducing a filler into the housing, said filled layer embedding at least the detection element and part of said attenuation member, wherein the attenuation member is an intervening member provided in a position surrounding the detection element between the housing and the detection element, and the intervening member has a predetermined number of holes.

14. The gas sensor as claimed in claim 13, wherein the intervening member surrounds the entire periphery of the detection element.

15. The gas sensor as claimed in claim 13, wherein the intervening member comprises a porous body.

16. The gas sensor as claimed in claim 13, wherein the intervening member is arranged in a position adjacent to the detection element.

17. A gas sensor including a detection element provided facing a predetermined flow path of a gas and receiving a predetermined signal causing the detection element to vibrate, and detecting means for transmitting a vibration wave having energy generated by vibration of the detection element in the flow path direction to detect characteristics of the gas, the gas sensor comprising:

a housing for housing the detection element in a form capable of transmitting the vibration wave for detection in the flow path direction;

an attenuation member, provided in the housing, for attenuating the energy of a vibration wave emitted in a direction different from the transmitting direction and colliding with the attenuation member; and a filled layer formed by introducing a filler into the housing, said filled layer embedding at least the detection element and part of said attenuation member, wherein the attenuation member is an intervening member provided in a position surrounding the detection element between the housing and the detection element, the intervening member is arranged in a position adjacent to the detection element, and the gas sensor comprises a film which is mounted on an opening portion of the housing and which partitions the housing and the flow path, wherein a matching member, which is mounted on the film and transmits vibration of the detection element to the flow path via the film, and the detection element, which is mounted on a surface on the opposite side of a mounting surface of the matching member to the film, are housed in the housing, and the intervening member is provided in a position surrounding the detection element and the matching member between the housing and the matching member and the detection element.

18. The gas sensor as claimed in claim 17, wherein the intervening member surrounds the entire periphery of the detection element.

19. The gas sensor as claimed in claim 17,
wherein the intervening member comprises a porous body.

20. The gas sensor as claimed in claim 17,
wherein the intervening member comprises plural media having different densities.

21. A gas sensor including a detection element provided facing a predetermined flow path of a gas and receiving a predetermined signal causing the detection element to vibrate, and detecting means for transmitting a vibration wave having energy generated by vibration of the detection element in the flow path direction to detect characteristics of the gas, the gas sensor comprising:

a housing for housing the detection element in a form capable of transmitting the vibration wave for detection in the flow path direction;

an attenuation member, provided in the housing, for attenuating the energy of a vibration wave emitted in a direction different from the transmitting direction and colliding with the attenuation member; and a filled layer formed by introducing a filler into the housing, said filled layer embedding at least the detection element and part of said attenuation member, wherein the attenuation member is an intervening member provided in a position surrounding the detection element between the housing and the detection element, said gas sensor further comprising:

an additional attenuation member, which is a surface member provided on the surface of the detection element opposite the surface of the filled layer.

22. The gas sensor as claimed in claim 21,
wherein the intervening member surrounds the entire periphery of the detection element.

23. The gas sensor as claimed in claim 21,
wherein the intervening member comprises a porous body.

24. The gas sensor as claimed in claim 21,
wherein the intervening member is arranged in a position adjacent to the detection element.

25. A gas sensor including a detection element provided facing a predetermined flow path of a gas and receiving a predetermined signal causing the detection element to vibrate, and detecting means for transmitting a vibration wave having energy generated by vibration of the detection element in the flow path direction to detect characteristics of the gas, the gas sensor comprising:

a housing for housing the detection element in a form capable of transmitting the vibration wave for detection in the flow path direction;

a reflecting section for reflecting the vibration wave for detection, which is transmitted from one detection element in the flow path direction, to a direction of the detection element;

an attenuation member, provided in the housing, for attenuating the energy of a vibration wave emitted in a direction different from the transmitting direction and colliding with the attenuation member; and a filled layer formed by introducing a filler into the housing, said filled layer embedding at least the detection element and part of said attenuation member, wherein the attenuation member is an intervening member provided in a position surrounding the detection element between the housing and the detection element, and said detecting means detecting characteristics of the gas based on the vibration wave for detection reflected by the reflecting section and received by said one detection element.

26. The gas sensor as claimed in claim 25,
wherein the intervening member surrounds the entire periphery of the detection element.

27. The gas sensor as claimed in claim 25,
wherein the intervening member comprises a porous body.

28. The gas sensor as claimed in claim 25,
wherein the intervening member is arranged in a position adjacent to the detection element.

* * * * *